United States Patent
Yoshida et al.

(10) Patent No.: US 6,211,227 B1
(45) Date of Patent: *Apr. 3, 2001

(54) TRICYCLIC COMPOUNDS

(75) Inventors: Makoto Yoshida; Takashi Seishi; Shigeru Aono; Tsuyoshi Yamagata; Kaoru Atsuki, all of Shizuoka; Toshiaki Kumazawa, Hachiohji; Haruki Takai, Yokohama; Koji Suzuki, Mishima; Akira Karasawa, Shizouka, all of (JP)

(73) Assignee: Kyowa Hakko Kogyo Co., Ltd., Tokyo (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/417,626

(22) Filed: Oct. 14, 1999

Related U.S. Application Data

(63) Continuation-in-part of application No. PCT/JP98/01713, filed on Apr. 15, 1998.

(30) Foreign Application Priority Data

Apr. 15, 1997 (JP) ..................................... 9-723397

(51) Int. Cl.$^7$ .......................... A61K 31/38; A61K 31/44; A61K 31/42; C07D 337/12; C07D 455/04

(52) U.S. Cl. .......................... 514/431; 514/291; 514/375; 549/12; 546/80; 548/218

(58) Field of Search ............................ 349/12; 514/431, 514/291, 375; 546/80; 548/218

(56) References Cited

U.S. PATENT DOCUMENTS

| | | | |
|---|---|---|---|
| 3,946,036 | 3/1976 | Gadient | 260/327 |
| 4,645,748 | 2/1987 | Hurwitz et al. | 436/509 |
| 5,116,863 | 5/1992 | Oshima et al. | 514/450 |
| 5,272,163 | 12/1993 | Russell et al. | 514/347 |
| 5,382,598 | 1/1995 | Keith et al. | 514/522 |
| 5,474,999 | 12/1995 | Russell et al. | 514/256 |
| 5,565,465 | 10/1996 | Russell et al. | 514/269 |
| 5,565,477 | 10/1996 | Russell et al. | 514/346 |
| 5,567,735 | 10/1996 | Russell et al. | 514/628 |
| 5,684,198 | 11/1997 | Russell et al. | 564/202 |
| 5,726,325 | 3/1998 | Yoshida et al. | 549/48 |
| 5,767,120 * | 6/1998 | Ting et al. | 514/255 |

OTHER PUBLICATIONS

J. Med. Chem., 1996, 39, pp. 4592–4601.
Journal of Medicinal Chemistry, 1978, vol. 21, No. 6, pp. 529–536.
Monatahefte fur Chemie 105, 1057—1066 (1974).

\* cited by examiner

*Primary Examiner*—Deborah C. Lambkin
(74) *Attorney, Agent, or Firm*—Fitzpatrick, Cella, Harper & Scinto

(57) ABSTRACT

The present invention provides tricyclic compounds which are useful for the treatment of pollakiuria and urinary incontinence and which are represented by general formula (I):

(wherein $R^1$ represents hydrogen, substituted or unsubstituted lower alkyl, etc.; $X^1$—$X^2$—$X^3$ represents $CR^5$=$CR^6$—$CR^7$=$CR^8$ (wherein $R^5$, $R^6$, $R^7$ and $R^8$, which may be the same or different, each represents hydrogen, substituted or unsubstituted lower alkyl, hydroxy, substituted or unsubstituted lower alkoxy, etc.), $N(O)m$=$CR^5$—$CR^6$=$CR^7$ (wherein $R^5$, $R^6$ and $R^7$ have the same significances as defined above, and m represents 0 or 1), S—$CR^7$=$CR^8$ (wherein $R^7$ and $R^8$ have the same significances as defined above), etc.;

and when $R^2$ represents hydrogen, substituted or unsubstituted lower alkyl, substituted or unsubstituted lower alkoxy, a substituted or unsubstituted N-substituted heterocyclic group, (wherein n is 0 or 1; $R^3$ and $R^4$, which may be the same or different, each represents hydrogen, substituted or unsubstituted lower alkyl, trifluoromethyl, etc., or $R^3$ and $R^4$ may be combined together to form cyclic alkyl; and Q represents hydroxy, halogen, etc.), etc., Y represents —$CH_2SO_2$—, —$SCH_2$—, —$SOCH_2$—, —$SO_2CH_2$—, etc.) and pharmaceutically acceptable salts thereof.

15 Claims, No Drawings

TRICYCLIC COMPOUNDS

CROSS-REFERENCE TO RELATED APPLICATION

This is a continuation-in-part of PCT/JP98/01713 filed on Apr. 15, 1998.

TECHNICAL FIELD

The present invention relates to tricyclic compounds having an activity to prolong the intervals between micturitions caused when a bladder becomes full, and pharmaceutically acceptable salts thereof. The compounds are useful for the treatment or alleviation of pollakiuria, urinary incontinence, urinary urgency or the sense of residual urine caused by various kinds of diseases or conditions such as neurogenic bladder and unstable bladder.

BACKGROUND ART

Japanese Published Unexamined Patent Application No. 286915/93 (EP524781) discloses N-substituted propanamide derivatives which are useful for the treatment of urinary incontinence.

DISCLOSURE OF THE INVENTION

An object of the present invention is to provide novel tricyclic compounds which are useful as therapeutic agents for pollakiuria and urinary incontinence.

The present invention relates to tricyclic compounds represented by general formula (I):

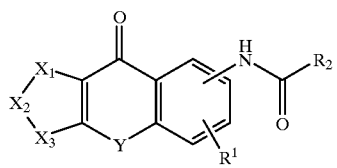

(I)

(wherein $R^1$ represents hydrogen, substituted or unsubstituted lower alkyl, substituted or unsubstituted lower alkoxy or halogen;

$X^1$—$X^2$—$X^3$ represents $CR^5$=$CR^6$—$CR^7$=$CR^8$ (wherein $R^5$, $R^6$, $R^7$ and $R^8$, which may be the same or different, each represents hydrogen, substituted or unsubstituted lower alkyl, hydroxy, substituted or unsubstituted lower alkoxy, nitro, amino, lower monoalkyl-substituted amino, lower dialkyl-substituted amino, substituted or unsubstituted lower alkanoylamino or halogen), $N(O)m$=$CR^5$—$CR^6$=$CR^7$ (wherein $R^5$, $R^6$ and $R^7$ have the same significances as defined above, and m represents 0 or 1), $CR^5$=$CR^6$—$N(O)m$=$CR^7$ (wherein $R^5$, $R^6$, $R^7$ and m have the same significances as defined above), $CR^5$=$CR^6$—$CR^7$=$N(O)m$ (wherein $R^5$, $R^6$, $R^7$ and m have the same significances as defined above), $CR^5$=$CR^6$—O (wherein $R^5$ and $R^6$ have the same significances as defined above), $CR^5$=$CR^6$—S (wherein $R^5$ and $R^6$ have the same significances as defined above), O—$CR^7$=$CR^8$ (wherein $R^7$ and $R^8$ have the same significances as defined above), S—$CR^7$=$CR^8$ (wherein $R^7$ and $R^8$ have the same significances as defined above) or O—$CR^7$=N (wherein $R^7$ has the same significance as defined above);

and when $R^2$ represents hydrogen, substituted or unsubstituted lower alkyl, substituted or unsubstituted lower alkenyl, trifluoromethyl, substituted or unsubstituted lower alkoxy, amino, substituted or unsubstituted lower monoalkyl-substituted amino, substituted or unsubstituted lower dialkyl-substituted amino, substituted or unsubstituted aryl, substituted or unsubstituted heteroaryl, substituted or unsubstituted aralkylamino, substituted or unsubstituted arylamino, a substituted or unsubstituted alicyclic heterocyclic group, a substituted or unsubstituted N-substituted heterocyclic group or

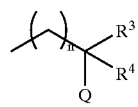

(wherein n is 0 or 1; $R^3$ and $R^4$, which may be the same or different, each represents hydrogen, substituted or unsubstituted lower alkyl, substituted or unsubstituted cyclic alkyl, substituted or unsubstituted aryl, substituted or unsubstituted aralkyl or trifluoromethyl, or $R^3$ and $R^4$ may be combined together to form cyclic alkyl; and Q represents hydroxy, substituted or unsubstituted lower alkoxy, amino or halogen);

Y represents —$CH_2SO_2$—, —$SCH_2$—, —$SOCH_2$— or —$SO_2CH_2$—, when $R^2$ represents hydrogen, substituted or unsubstituted lower alkenyl, trifluoromethyl, substituted or unsubstituted lower alkoxy, amino, substituted or unsubstituted lower monoalkyl-substituted amino, substituted or unsubstituted lower dialkyl-substituted amino, substituted or unsubstituted aryl, substituted or unsubstituted heteroaryl, substituted or unsubstituted aralkylamino, substituted or unsubstituted arylamino, a substituted or unsubstituted alicyclic heterocyclic group, a substituted or unsubstituted N-substituted heterocyclic group or

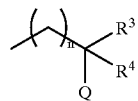

(wherein n, $R^3$, $R^4$ and Q have the same significances as defined above),

Y represents —$OCH_2$—);

and pharmaceutically acceptable salts thereof.

Hereinafter, the compounds represented by general formula (I) are referred to as Compounds (I), and the same applies to the compounds of other formula numbers.

In the definitions of each group in general formula (I), the lower alkyl includes straight-chain or branched alkyl groups having 1 to 6 carbon atoms, such as methyl, ethyl, propyl, isopropyl, butyl, isobutyl, sec-butyl, tert-butyl, pentyl, hexyl, 1,2,2-trimethylpropyl and the like. The halogen means fluorine, chlorine, bromine or iodine. The alkyl moiety of the lower alkoxy, the lower monoalkyl-substituted amino and the lower dialkyl-substituted amino has the same significance as the above lower alkyl. The lower alkanoyl of the lower alkanoylamino includes alkanoyl groups having 1 to 6 carbon atoms, such as formyl, acetyl, propanoyl, butanoyl, pentanoyl, 2,2-dimethylpropanoyl and the like. The lower alkenyl includes straight-chain or branched alkenyl groups having 2 to 6 carbon atoms, such as vinyl, allyl, 1-propenyl, methacryl, 1-butenyl, crotyl, pentenyl, hexenyl and the like. The aryl includes phenyl, naphthyl and the like, and the heteroaryl includes pyridyl, furyl, thienyl, quinolyl, imidazolyl, benzimidazolyl, thiazolyl and the like. The aralkyl includes aralkyl groups having 7 to 12 carbon atoms, such as benzyl, phenethyl, naphthylmethyl and the like. The alicyclic heterocyclic group includes tetrahydrofuryl, tetrahydrothienyl, chromanyl and the like. The N-substituted heterocyclic group is a heterocyclic ring containing 1 to 2 nitrogen atoms therein, which may contain hetero atoms such as O and S, said nitrogen atom being bonded to the adjoining carbonyl group. The N-substituted heterocyclic group includes, for example, pyrrolidinyl, piperazinyl, piperidino, morpholino, thiomorpholino and oxazolyl. The cyclic alkyl includes cyclic alkyl groups having 3 to 8 carbon atoms, such as cyclopropyl, cyclobutyl, cyclopentyl, cyclohexyl, cycloheptyl, cyclooctyl and the like.

The substituted lower alkyl, the substituted lower alkoxy, the substituted lower monoalkyl-substituted amino, the substituted lower dialkyl-substituted amino, the substituted lower alkanoylamino, the substituted lower alkenyl and the substituted cyclic alkyl each has 1 to 3 substituents which are the same or different. Examples of the substituents are hydroxy, halogen, nitro, amino, lower monoalkyl-substituted amino, lower dialkyl-substituted amino and lower alkoxy. The halogen has the same significance as defined above. The alkyl group of the lower monoalkyl-substituted amino, the lower dialkyl-substituted amino and the lower alkoxy has the same significance as the above lower alkyl.

The substituted aryl, the substituted heteroaryl, the substituted aralkyl, the substituted aralkylamino and the substituted arylamino each has 1 to 3 substituents which are the same or different. Examples of the substituents are lower alkyl, hydroxy, amino and halogen. The lower alkyl and halogen have the same significances as the above lower alkyl and halogen, respectively.

The substituted alicyclic heterocyclic group and the substituted N-substituted heterocyclic group each has 1 to 3 substituents which are the same or different. Examples of the substituents are lower alkyl, hydroxy and halogen. The lower alkyl and halogen have the same significances as the above lower alkyl and halogen, respectively.

As $R^1$, hydrogen, substituted or unsubstituted lower alkoxy and halogen are preferred. Particularly preferred is hydrogen.

As Y, —$CH_2SO_2$—, —$SO_2CH_2$— and —$OCH_2$— are preferred. Particularly preferred is —$CH_2SO_2$—.

As $X^1$—$X^2$—$X^3$, S—$CR^7$=$CR^8$ (wherein $R^7$ and $R^8$ have the same significances as defined above) and $CR^5$=$CR^6$—$CR^7$=$CR^8$ (wherein $R^5$, $R^6$, $R^7$ and $R^8$ have the same significances as defined above) are preferred. Particularly preferred is S—$CR^7$=$CR^8$ (wherein $R^7$ and $R^8$ have the same significances as defined above).

As $R^2$,

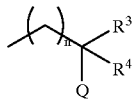

(wherein n, $R^3$, $R^4$ and Q have the same significances as defined above) is preferred. Particularly preferred is

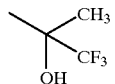

The pharmaceutically acceptable salts of Compounds (I) include pharmaceutically acceptable acid addition salts. Examples of the pharmaceutically acceptable acid addition salts are inorganic acid addition salts such as hydrochloride, hydrobromide, hydroiodide, nitrate, sulfate, phosphate and the like, and organic acid addition salts such as formate, acetate, benzoate, maleate, fumarate, succinate, tartrate, citrate, oxalate, glyoxylate, aspartate, methanesulfonate, ethanesulfonate, benzenesulfonate and the like.

The production methods for preparing Compounds (I) are described below.

Process 1

Compound (Ia), i.e., Compound (I) in which Y is —$OCH_2$—, and Compound (Ib), i.e., Compound (I) in which Y is —$SCH_2$—, can be prepared according to the following reaction steps.

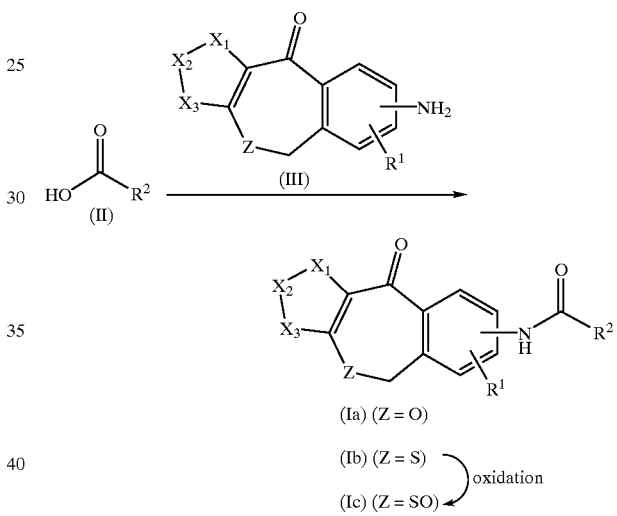

(In the formulae, Z represents O or S, and $R^1$, $R^2$ and $X^1$—$X^2$—$X^3$ have the same significances as defined above.)

Compound (Ia) and Compound (Ib) can be obtained by treating Compound (II) with an equivalent amount of a halogenating agent such as thionyl chloride or oxalyl chloride in an inert solvent such as dichloromethane, dichloroethane, tetrachloroethane or dimethylacetamide at a temperature between −20° C. and 0° C. for 5 minutes to 12 hours, and then subjecting the obtained substance to reaction with Compound (III) at a temperature between 0° C. and the boiling point of the solvent used for 5 minutes to 24 hours, or by reacting commercially available acid anhydride or acid chloride which is corresponding to Compound (II) with Compound (III) under the above conditions.

Compound (Ic), i.e., Compound (I) in which Y is —$SOCH_2$— can also be obtained by treating Compound (Ib), i.e., Compound (I) in which Y is —$SCH_2$— with an equivalent amount of an oxidizing agent such as 3-chloroperbenzoic acid in a solvent such as dichloromethane or chloroform at a temperature between 0° C. and the boiling point of the solvent used for 1 to 24 hours according to a known method.

The starting Compound (II) may be a commercially available one or can be prepared according to the procedure described in J. Chem. Soc., 2329 (1951). The starting Compound (III) can be prepared according to the procedure described in the following process 2.

Process 2

Compound (III) can be prepared according to the following reaction steps.

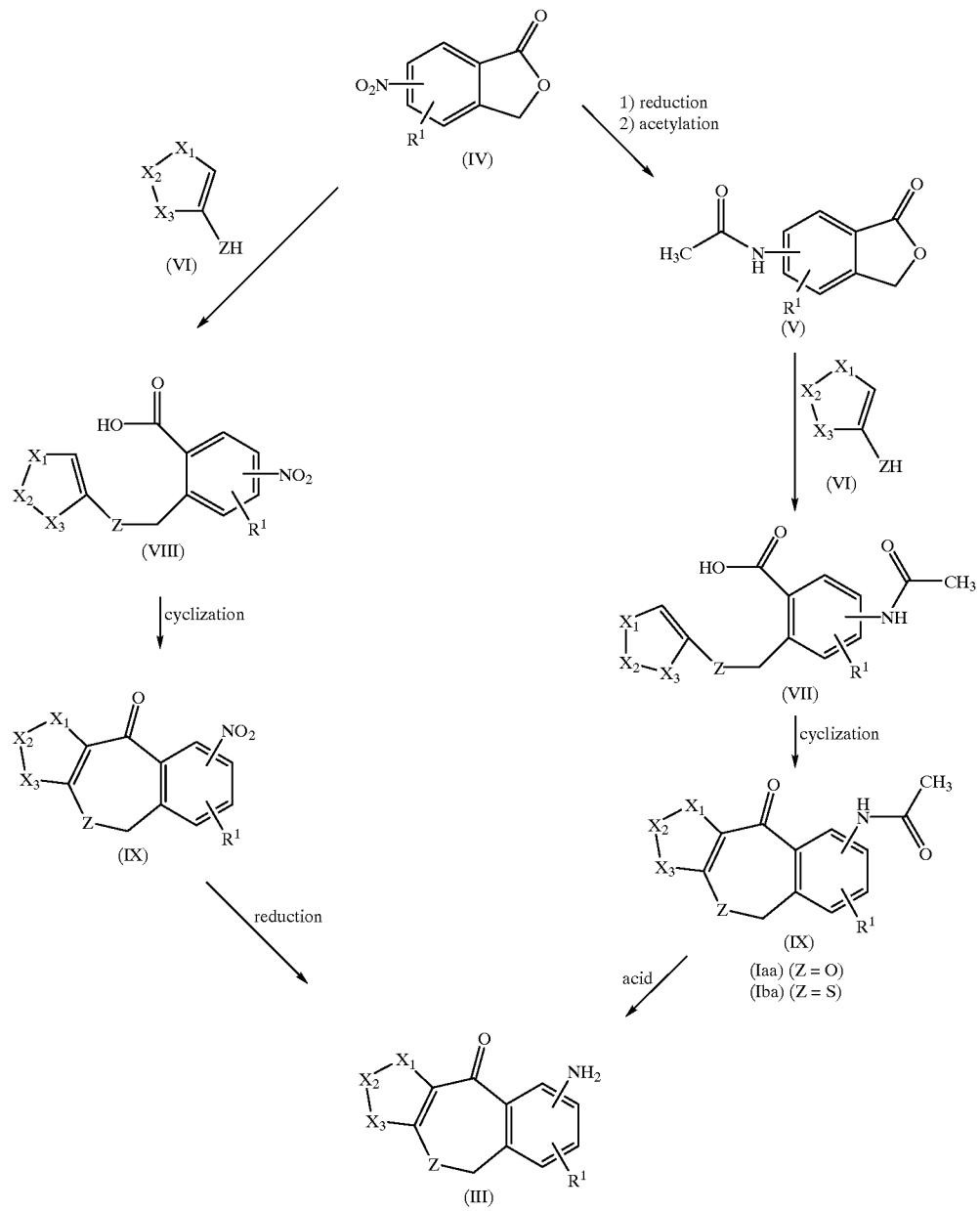

(In the formulae, $R^1$, $X^1$—$X^2$—$X^3$ and Z have the same significances as defined above.)

Compound (V) can be obtained by reducing the nitro group of Compound (IV) with a reducing agent such as reduced iron in a mixed solvent of water and a solvent such as methanol or ethanol at a temperature between room temperature and the boiling point of the solvent used for 1 to 24 hours, and then subjecting the obtained amine to reaction with an acetylating agent such as acetic anhydride or acetyl chloride in an inert solvent such as tetrahydrofuran, dioxane, dimethylformamide, dimethylacetamide or dichloromethane in the presence of a base such as pyridine, triethylamine or diisopropylethylamine at a temperature between 0° C. and the boiling point of the solvent used for 1 to 24 hours. The starting Compound (IV) may be a commercially available one or can be prepared according to the procedure described in J. Org. Chem., vol. 52, 129 (1987), Syn. Commun., vol. 24, 1789 (1994), etc.

Compound (VII) can be obtained by heating Compound (V) and a sodium salt prepared from Compound (VI) without a solvent, or by subjecting Compound (V) to reaction with said sodium salt in an inert solvent such as tetrahydrofuran, dimethylformamide, dimethylacetamide, dimethyl sulfoxide, toluene or xylene at a temperature between 0° C. and the boiling point of the solvent used for 1 to 24 hours.

Compound (Iaa), i.e., Compound (I) in which Y is —OCH$_2$— and R$^2$ is a methyl group and Compound (Iba), i.e., Compound (I) in which Y is —SCH$_2$ and R$^2$ is a methyl group can be prepared by treating Compound (VII) with trifluoroacetic anhydride in an inert solvent such as dichloromethane, 1,2-dichloroethane, tetrachloroethane, nitrobenzene, carbon disulfide or o-dichlorobenzene at a temperature between −15° C. and room temperature according to the method described in Japanese Published Unexamined Patent Application No. 91040/90 (EP345747), etc. to give the corresponding acid anhydride, and then subjecting the obtained acid anhydride to ring closure reaction without isolation from the solvent in the presence of 0.1 to one equivalent of a Lewis acid such as boron trifluoride diethyl etherate, aluminum chloride or titanium tetrachloride, or a protonic acid such as sulfuric acid, trifluoroacetic acid, methanesulfonic acid or trifluoromethanesulfonic acid at a temperature between 0° C. and the boiling point of the solvent used.

Compound (III) can be obtained by heating under reflux Compound (Iaa) or Compound (Iba) in a mixed solvent of water and a solvent such as methanol or ethanol, or without a solvent, in the presence of concentrated hydrochloric acid.

Compound (III) can also be synthesized by carrying out the above reactions in a different order. That is, Compound (VIII) can be obtained by reacting Compound (IV) with a sodium salt prepared from Compound (VI) according to the method for obtaining Compound (VII) from Compound (V). Compound (IX) can be obtained by subjecting Compound (VIII) to ring closure reaction according to the method for obtaining Compound (Iaa) and Compound (Iba) from Compound (VII). Compound (III) can be obtained by reducing the nitro group of Compound (IX) according to the method for reducing the nitro group of Compound (IV).

Process 3

Compound (VII) can also be prepared according to the following reaction steps.

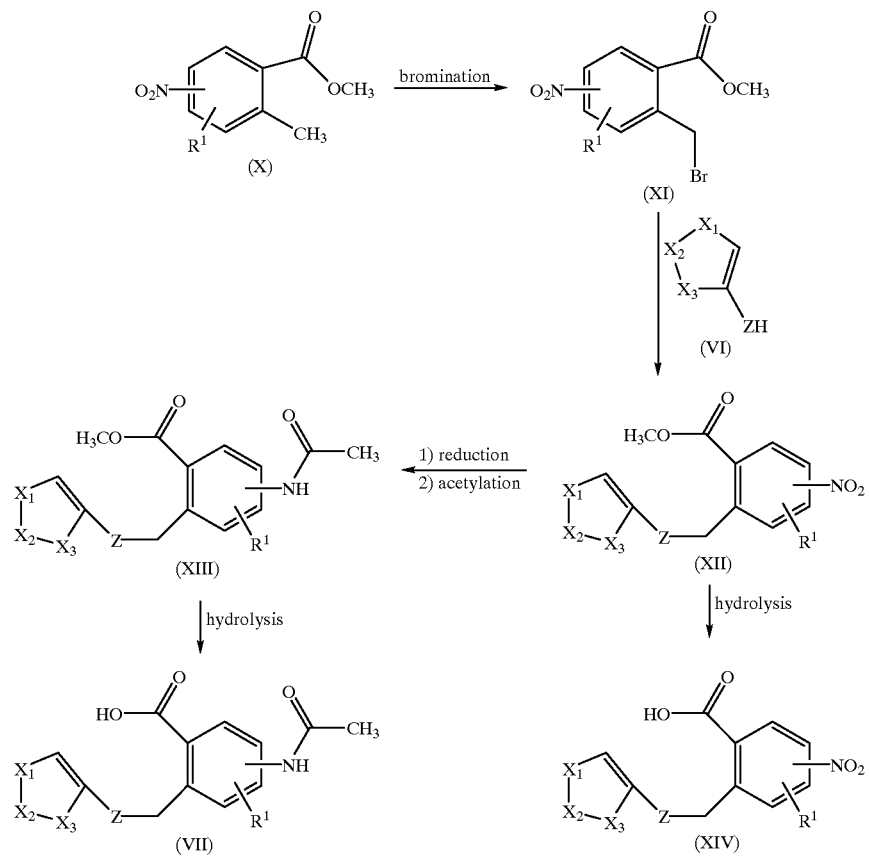

(In the formulae, R$^1$, X$^1$—X$^2$—X$^3$ and Z have the same significances as defined above.)

Compound (XI) can be obtained by heating under reflux the corresponding starting material (X) which Is commercially available such as ethyl 2nitro-6-methylbenzoate in a solvent such as carbon tetrachloride or 1,2-dichloroethane in the presence of a radical initiator such as azobisisobutyronitrile (AIBN) and a brominating agent such as N-bromosuccinimide (NBS) for 1 to 24 hours according to a known method.

Compound (XII) can be obtained by subjecting Compound (XI) to reaction with Compound (VI) in an inert solvent such as dichloromethane, tetrahydrofuran, dimethylformamide, dimethylacetamide or dimethylsulfoxide in the presence of a base such as triethylamine, sodium methoxide or potassium carbonate at a temperature between −20° C. and the boiling point of the solvent used for 1 to 24 hours.

Compound (XIII) can be obtained by reducing the nitro group of Compound (XII) with a reducing agent such as reduced iron in a mixed solvent of water and a solvent such as methanol or ethanol at a temperature between room temperature and the boiling point of the solvent used for 1 to 24 hours, and then subjecting the obtained amine to reaction with an acetylating agent such as acetic anhydride or acetyl chloride in an inert solvent such as tetrahydrofuran, dimethylformamide, dimethylacetamide or dichloromethane in the presence of a base such as pyridine, triethylamine or dulsopropylamine at a temperature between 0° C. and the boiling point of the solvent used for 1 to 24 hours.

Compound (VII) can be obtained by hydrolyzing Compound (XIII) in a mixed solvent of water and a solvent such as methanol, ethanol, dioxane or tetrahydrofuran in the presence of a base such as lithium hydroxide, sodium hydroxide or potassium hydroxide at a temperature between room temperature and the boiling point of the solvent used for 5 minutes to 24 hours.

Compound (XIV) can be obtained by treating Compound (XII) according to the method by which Compound (VII) was obtained from Compound (XIII).

Process 4

Compound (Id), i.e., Compound (I) in which Y is —CH$_2$SO$_2$—, and Compound (Ie), i.e., Compound (I) in which Y is —SO$_2$CH$_2$— can be prepared according to the following reaction steps.

When $X^1$—$X^2$—$X^3$ in Compound (XV) or Compound (Ib) is N=CR$^5$—CR$^6$=CR$^7$ (wherein R$^5$, R$^6$ and R$^7$ have the same significances as defined above), CR$^5$=CR$^6$—N=CR$^7$ (wherein R$^5$, R$^6$ and R$^7$ have the same significances as defined above) or CR$^5$=CR$^6$—CR$^7$=N (wherein R$^5$, R$^6$ and R$^7$ have the same significances as defined above), Compound (Id) or Compound (Ie) in which the nitrogen atom in the ring is oxidized, that is, $X^1$—$X^2$—$X^3$ is represented by NO=CR$^5$—CR$^6$=CR$^7$ (wherein R$^5$, R$^6$ and R$^7$ have the same significances as defined above), CR$^5$=CR$^6$—NO=CR$^7$ (wherein R$^5$, R$^6$ and R$^7$ have the same significances as defined above) or CR$^5$=CR$^6$—CR$^7$=NO (wherein R$^5$, R$^6$ and R$^7$ have the same significances as defined above) can be synthesized by varying the reaction conditions including the amount of the oxidizing agent to be used and the reaction temperature.

Process 5

Compound (XV) can be prepared according to the following reaction steps.

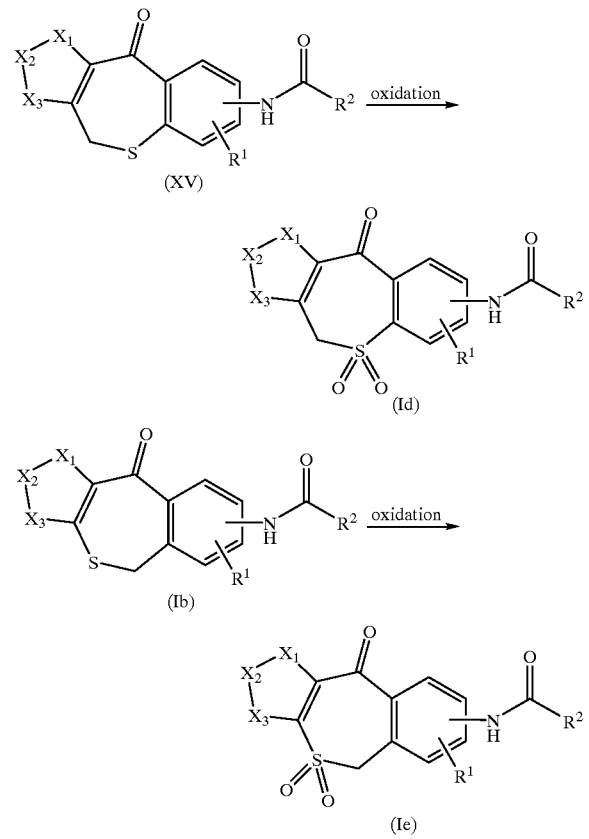

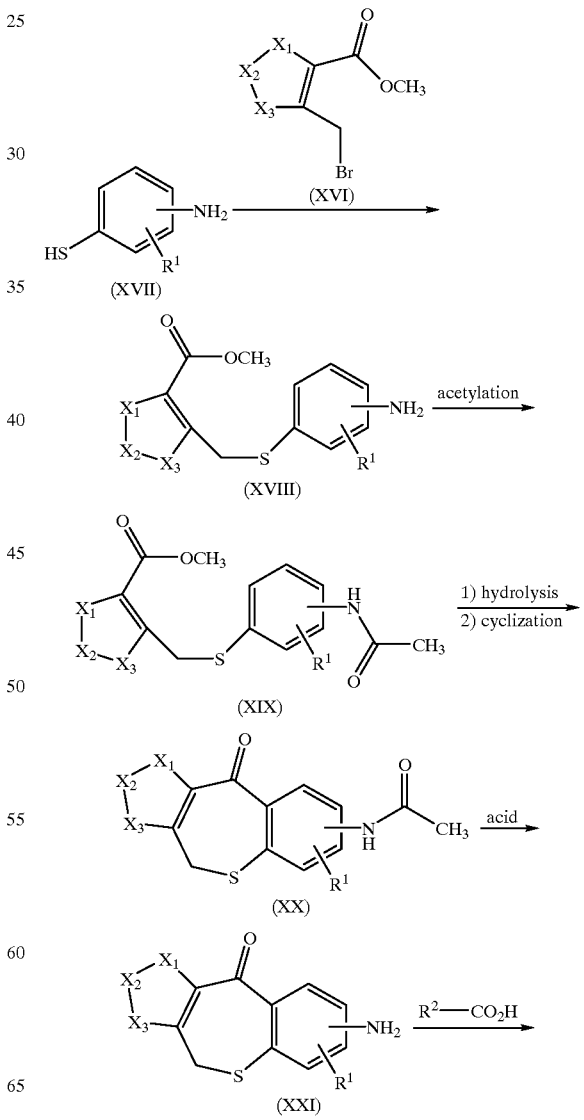

(In the formulae, R$^1$, R$^2$ and $X^1$—$X^2$—$X^3$ have the same significances as defined above.)

Compound (Id) or Compound (Ie) can be obtained by treating Compound (XV) or Compound (Ib) with 2 equivalents or more of an oxidizing agent such as 3-chloroperbenzoic acid or magnesium monoperoxyphthalate hexahydrate in an inert solvent such as dichloromethane, chloroform, 1,2-dichloroethane or 1,1,2,2-tetrachloroethane at a temperature between 0° C. and the boiling point of the solvent used for 1 to 24 hours.

-continued

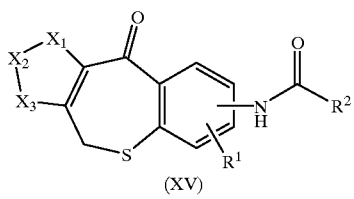

(XV)

(In the formulae, $R^1$, $R^2$ and $X^1$—$X^2$—$X^3$ have the same significances as defined above.)

Compound (XVI) can be obtained by heating under reflux the corresponding starting material such as methyl 2-methylbenzoate, methyl 2-methylnicotinate or methyl 3-methylthiophene-2-carboxylate in a solvent such as carbon tetrachloride or 1,2-dichloroethane in the presence of a radical initiator such as azobisisobutyronitrile (AIBN) and a brominating agent such as N-bromosuccinimide (NBS) for 1 to 24 hours according to a known method.

Compound (XVIII) can be obtained by subjecting a commercially available aminothiophenol derivative (XVII) such as 3-aminothiophenol to reaction with the above Compound (XVI) in an inert solvent such as dichloromethane, tetrahydrofuran, dimethylformamide, dimethylacetamide or dimethyl sulfoxide in the presence of a base such as triethylamine, sodium methoxide or potassium carbonate at a temperature between −20° C. and the boiling point of the solvent used for 1 to 24 hours.

Compound (XIX) can be obtained by subjecting Compound (XVIII) to reaction with an acetylating agent such as acetic anhydride or acetyl chloride in an inert solvent such as tetrahydrofuran, dioxane, dimethylformamide, dimethylacetamide, dichloromethane or dimethyl sulfoxide in the presence of a base such as pyridine, triethylamine or diisopropylethylamine at a temperature between −20° C. and the boiling point of the solvent used for 1 to 24 hours.

Compound (XX) can be obtained by first hydrolyzing Compound (XIX) in a mixed solvent of water and a solvent such as methanol, ethanol, dioxane or tetrahydrofuran in the presence of a base such as lithium hydroxide, sodium hydroxide or potassium hydroxide at a temperature between room temperature and the boiling point of the solvent used for 5 minutes to 24 hours; treating the obtained carboxylic acid with trifluoroacetic anhydride in an inert solvent such as dichloromethane, 1,2-dichloroethane, tetrachloroethane, nitrobenzene, carbon disulfide, nitromethane or o-dichlorobenzene at a temperature between −15° C. and room temperature according to the method described in Japanese Published Unexamined Patent Application No. 91040/90 (EP345747), etc. to give acid anhydride; and then subjecting the obtained acid anhydride to ring closure reaction without isolation from the solvent in the presence of 0.1 to one equivalent of a Lewis acid such as boron trifluoride diethyl etherate, aluminum chloride or titanium tetrachloride, or a protonic acid such as polyphosphoric acid, sulfuric acid, trifluoroacetic acid, methanesulfonic acid or trifluoromethanesulfonic acid at a temperature between 0° C. and the boiling point of the solvent used.

Compound (XXI) can be obtained by treating Compound (XX) according to the method for obtaining Compound (III) from Compound (Iaa) and Compound (Iba) in Process 2.

Compound (XV) can be obtained from Compound (XXI) according to the method described in Process 1. When $R^2$ is amino, substituted or unsubstituted lower monoalkyl-substituted amino, substituted or unsubstituted lower dialkyl-substituted amino, substituted or unsubstituted aralkylamino, substituted or unsubstituted arylamino, or a substituted or unsubstituted N-substituted heterocyclic group, the desired compound can be synthesized by first converting Compound (XXI) to the corresponding carbamate in an inert solvent such as tetrahydrofuran at a temperature between 0° C. and 25° C. by the use of phenyl chloroformate or p-nitrophenyl chloroformate according to the method described in J. Med. Chem.,vol. 39,304(1996), etc., and then subjecting the obtained carbamate to reaction with the corresponding amine at the same temperature.

The intermediates and the desired compounds in each process described above can be isolated and purified by purification methods conventionally used in synthetic organic chemistry, for example, filtration, extraction, washing, drying, concentration, recrystallization and various kinds of chromatography. The intermediates may be subjected to the subsequent reaction without purification.

There may be stereoisomers such as geometrical isomers and optical isomers for some of Compounds (I). All possible isomers including these isomers and mixtures thereof are within the scope of the present invention.

In the case where a salt of Compound (I) is desired and it is produced in the form of the desired salt, it can be subjected to purification as such. In the case where Compound (I) is produced in the free state and its salt is desired, Compound (I) is dissolved or suspended in a suitable solvent, and an acid is added thereto to form a salt, followed by isolation and purification.

Compounds (I) may exist in the form of adducts with water or various solvents, which are also within the scope of the present invention.

Examples of Compounds (I) are shown in Tables 1 to 3.

TABLE 1-1

| Compd. No. | R |
|---|---|
| 1-1 | (structure) |
| 1-2 | (structure) |

TABLE 1-1-continued
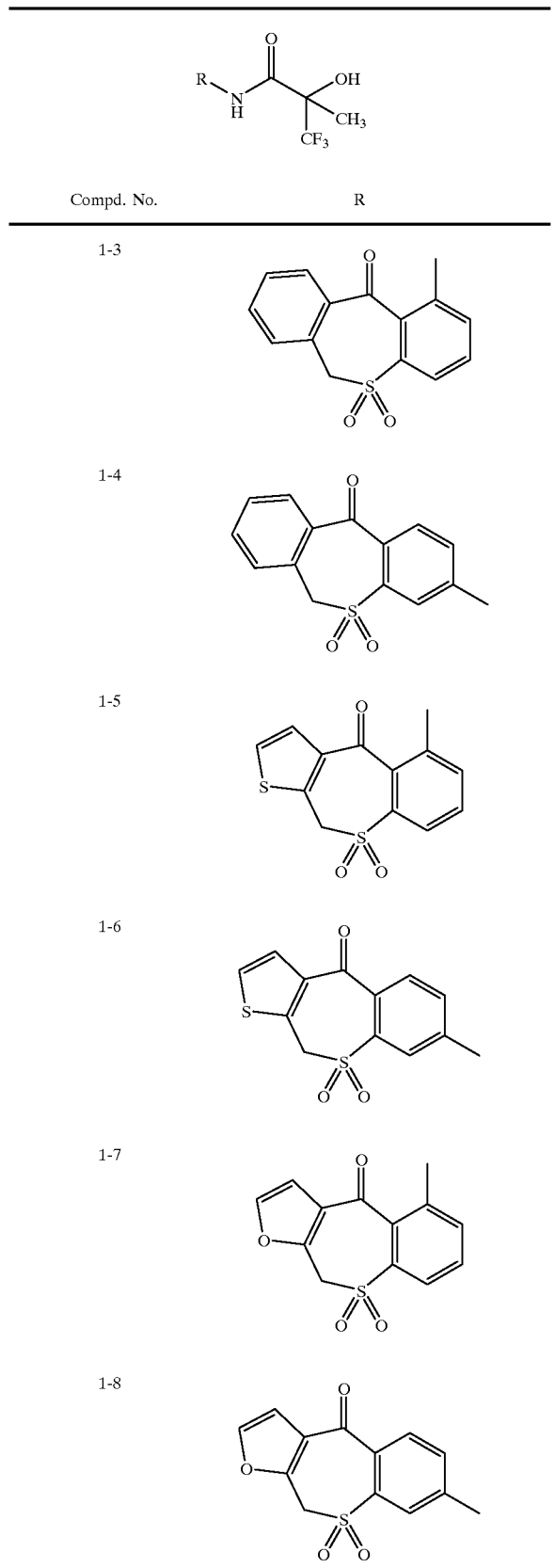
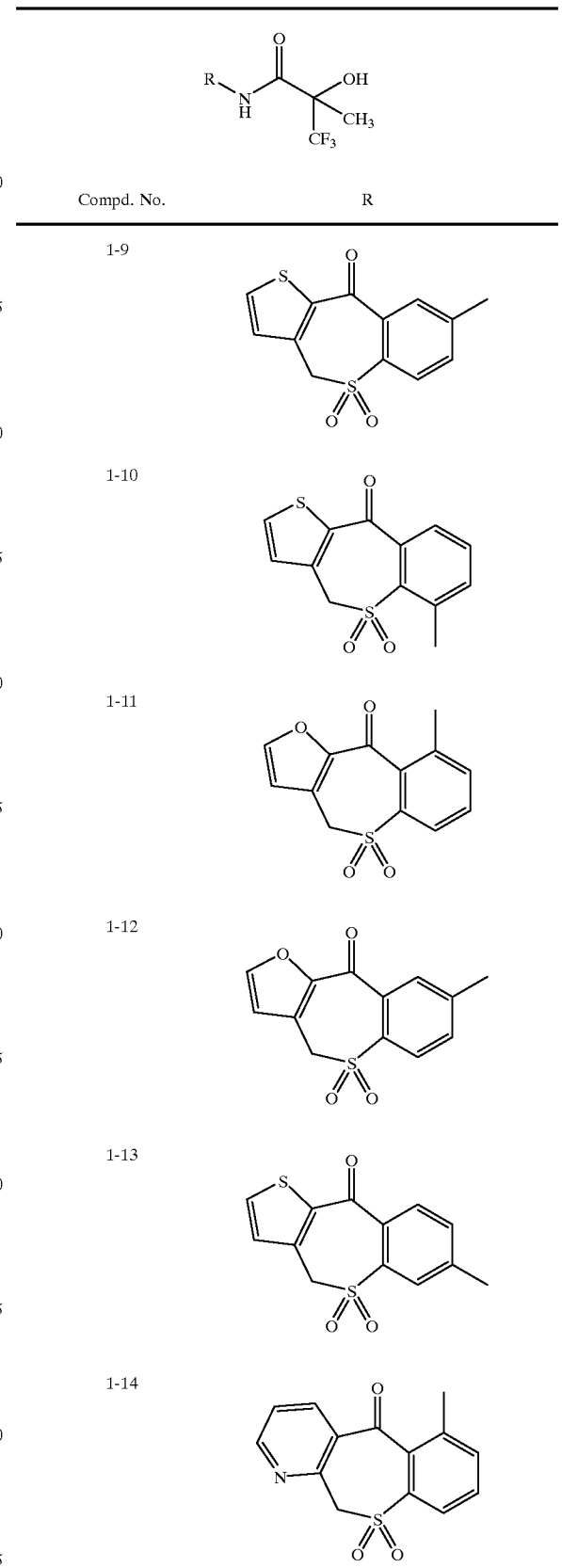

TABLE 1-1-continued
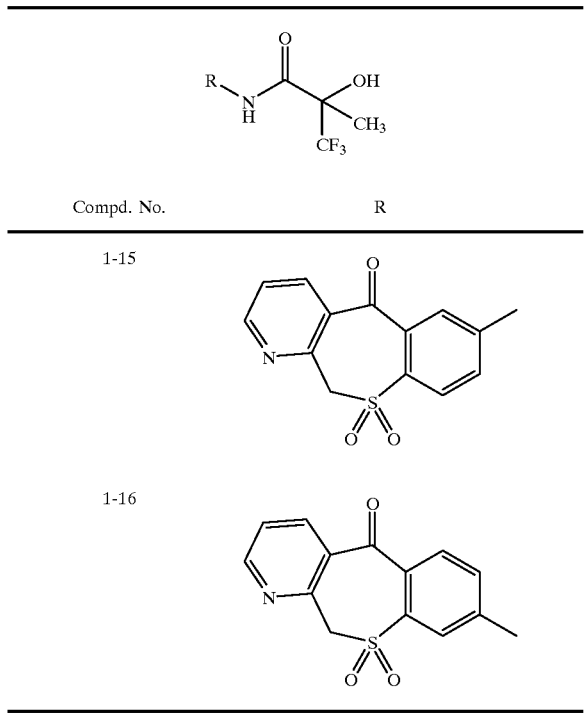
| Compd. No. | R |
|---|---|
| 1-15 | |
| 1-16 | |
TABLE 1-2
| Compd. No. | R |
|---|---|
| 1-17 | |
| 1-18 | |
| 1-19 | |
TABLE 1-2-continued
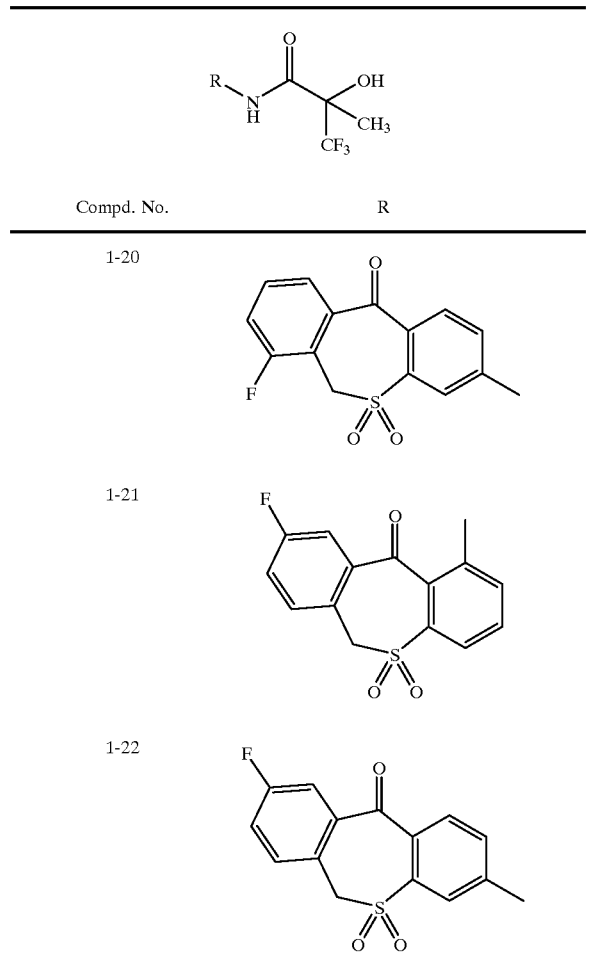
| Compd. No. | R |
|---|---|
| 1-20 | |
| 1-21 | |
| 1-22 | |
| 1-23 | |
| 1-24 | |
| 1-25* | |

TABLE 1-2-continued
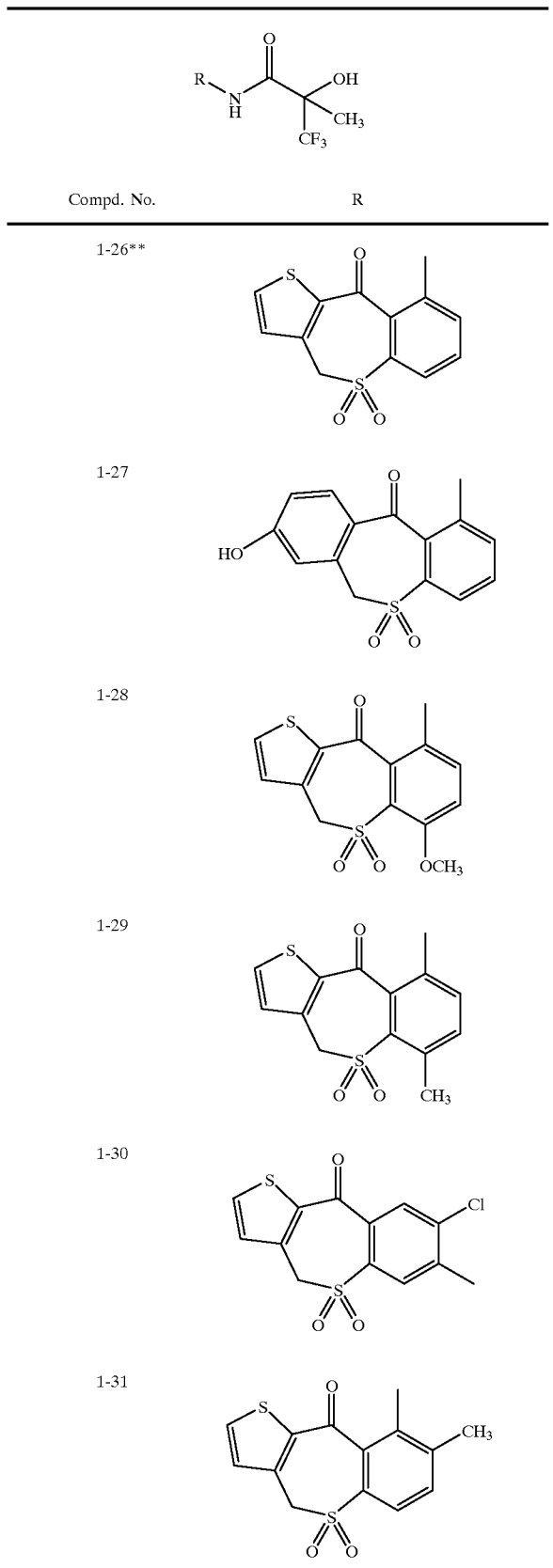
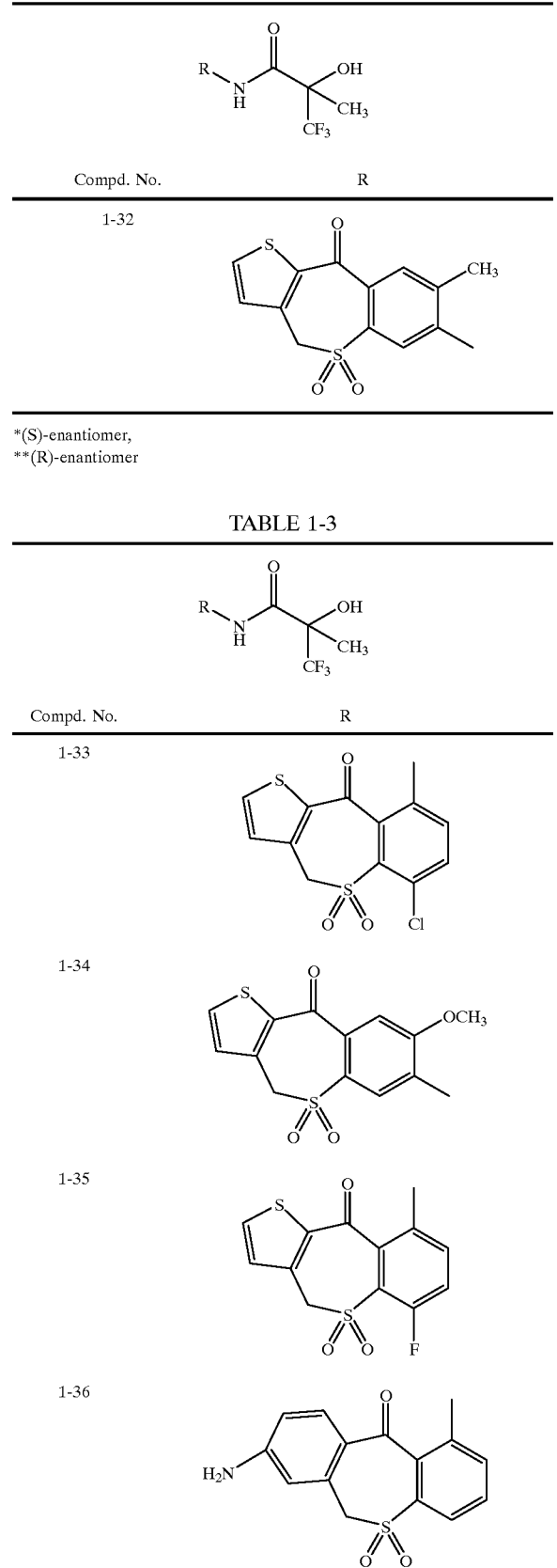
*(S)-enantiomer,
**(R)-enantiomer
TABLE 1-3

TABLE 1-3-continued
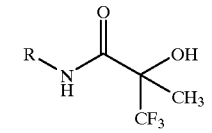
| Compd. No. | R |
|---|---|
| 1-37 | 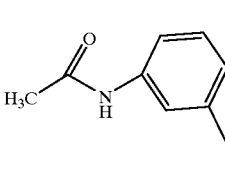 |
| 1-38 | 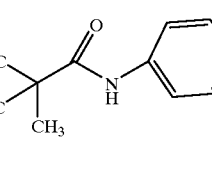 |
| 1-39 | 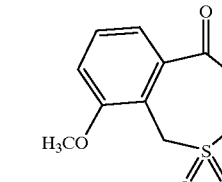 |
| 1-40 | 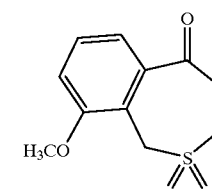 |
| 1-41 | 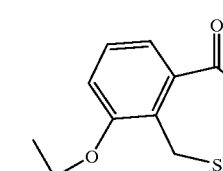 |
| 1-42 | 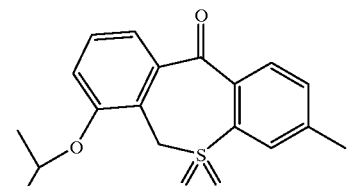 |
TABLE 1-3-continued
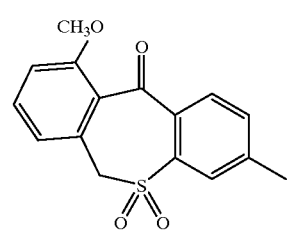
| Compd. No. | R |
|---|---|
| 1-43 | 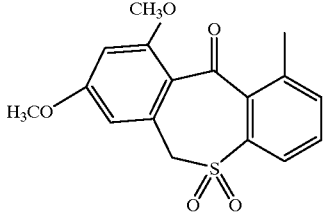 |
| 1-44 | 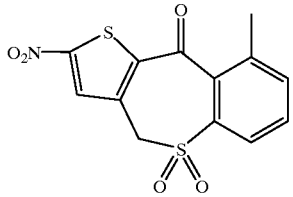 |
| 1-45 | 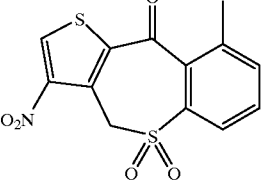 |
| 1-46* | 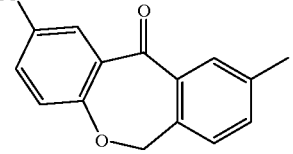 |
| 1-47* | |
| 1-48 | |
*(S)-enantiomer

TABLE 1-4

![structure: R-NH-C(=O)-C(OH)(CH3)(CF3)]

| Compd. No. | R |
|---|---|
| 1-49 | [dibenzo structure with H3CO, S, carbonyl, methyl] |
| 1-50 | [dibenzo structure with H3CO, SO2, carbonyl, methyl] |
| 1-51 | [dibenzo structure with SO2, carbonyl, methyl] |
| 1-52 | [dibenzo structure with SO2, carbonyl, methyl] |
| 1-53 | [pyridine N-oxide fused structure with SO2, carbonyl, methyl] |
| 1-54 | [pyridine N-oxide fused structure with SO2, carbonyl, methyl] |

TABLE 1-4-continued

![structure: R-NH-C(=O)-C(OH)(CH3)(CF3)]

| Compd. No. | R |
|---|---|
| 1-55 | [pyrido-fused structure with SO2, carbonyl, methyl] |

TABLE 2-1

![structure: R-NH-C(=O)-C(CH3)3]

| Compd. No. | R |
|---|---|
| 2-1 | [thieno-fused structure with SO2, carbonyl, methyl] |
| 2-2 | [thieno-fused structure with SO2, carbonyl, methyl] |
| 2-3 | [thieno-fused structure with SO2, carbonyl, dimethyl] |
| 2-4 | [thieno-fused structure with SO2, carbonyl, methyl, Cl] |

TABLE 2-1-continued
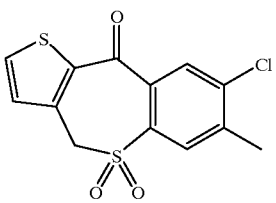
| Compd. No. | R |
|---|---|
| 2-5 | 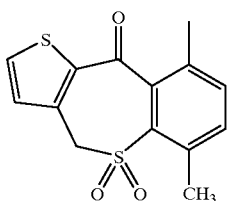 |
| 2-6 | 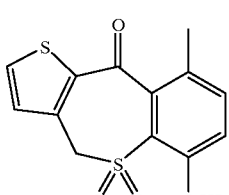 |
| 2-7 | 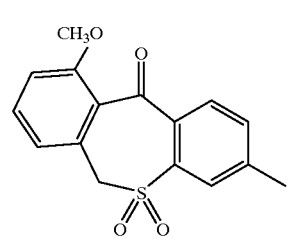 |
| 2-8 | 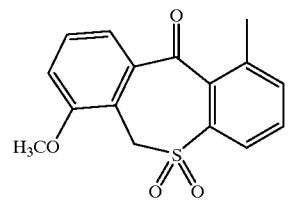 |
| 2-9 | 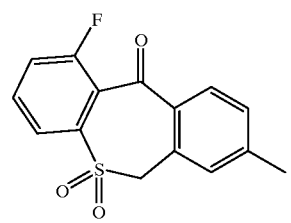 |
| 2-10 | 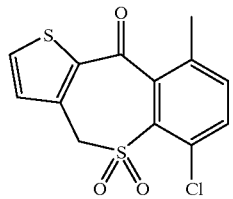 |
TABLE 2-1-continued
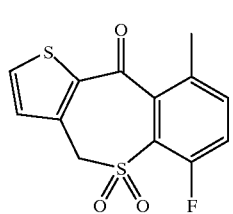
| Compd. No. | R |
|---|---|
| 2-11 | 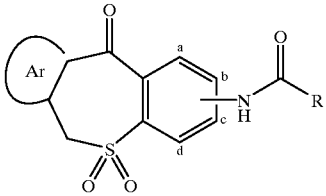 |
| 2-12 | 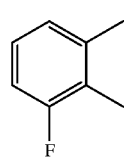 |
TABLE 3-1
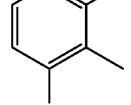
| Compd. No. | Ar | Position | R |
|---|---|---|---|
| 3-1 | 2,3-dimethylthiophene | a | —CH₃ |
| 3-2 | 2,3-dimethyl-1-fluorobenzene | a | —CH₃ |
| 3-3 | 2,3-dimethyl-1-fluorobenzene | c | —CH₃ |

TABLE 3-1-continued

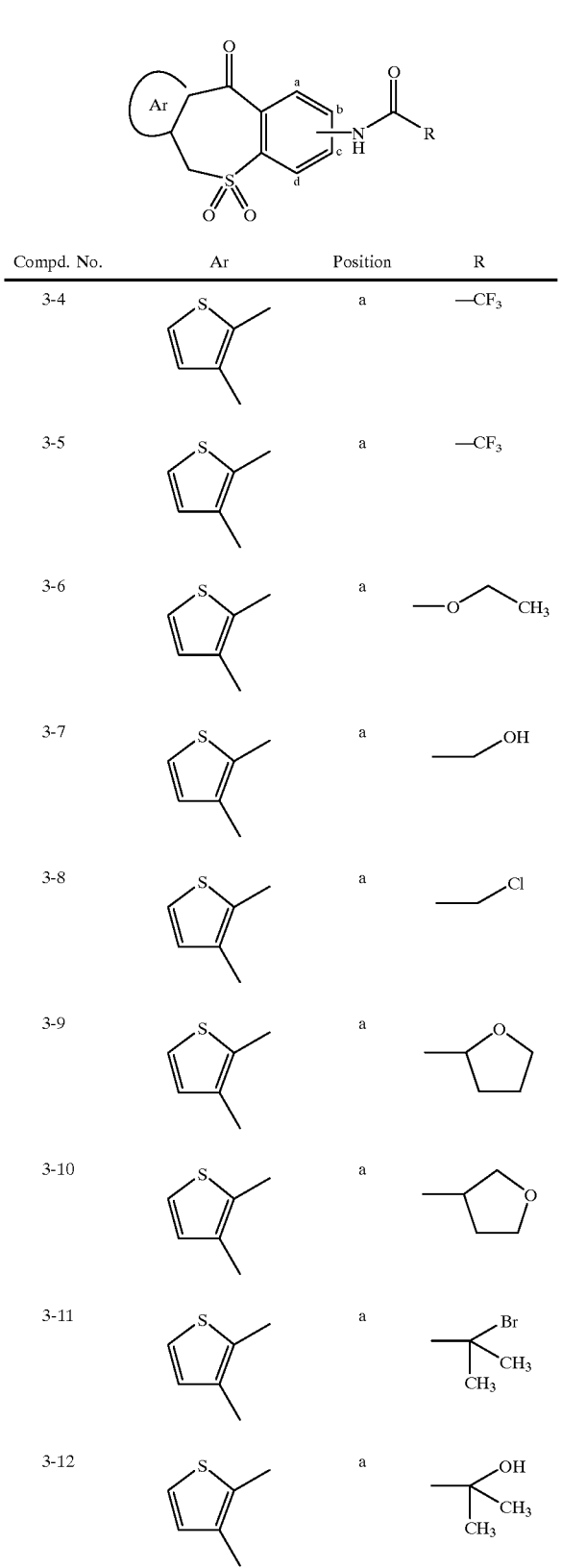

| Compd. No. | Ar | Position | R |
|---|---|---|---|
| 3-4 | 2,3-dimethylthiophene | a | —CF₃ |
| 3-5 | 2,3-dimethylthiophene | a | —CF₃ |
| 3-6 | 2,3-dimethylthiophene | a | —O—CH₂CH₃ |
| 3-7 | 2,3-dimethylthiophene | a | —CH₂OH |
| 3-8 | 2,3-dimethylthiophene | a | —CH₂Cl |
| 3-9 | 2,3-dimethylthiophene | a | tetrahydrofuran-2-yl |
| 3-10 | 2,3-dimethylthiophene | a | tetrahydrofuran-3-yl |
| 3-11 | 2,3-dimethylthiophene | a | —C(Br)(CH₃)CH₃ |
| 3-12 | 2,3-dimethylthiophene | a | —C(OH)(CH₃)CH₃ |

TABLE 3-1-continued

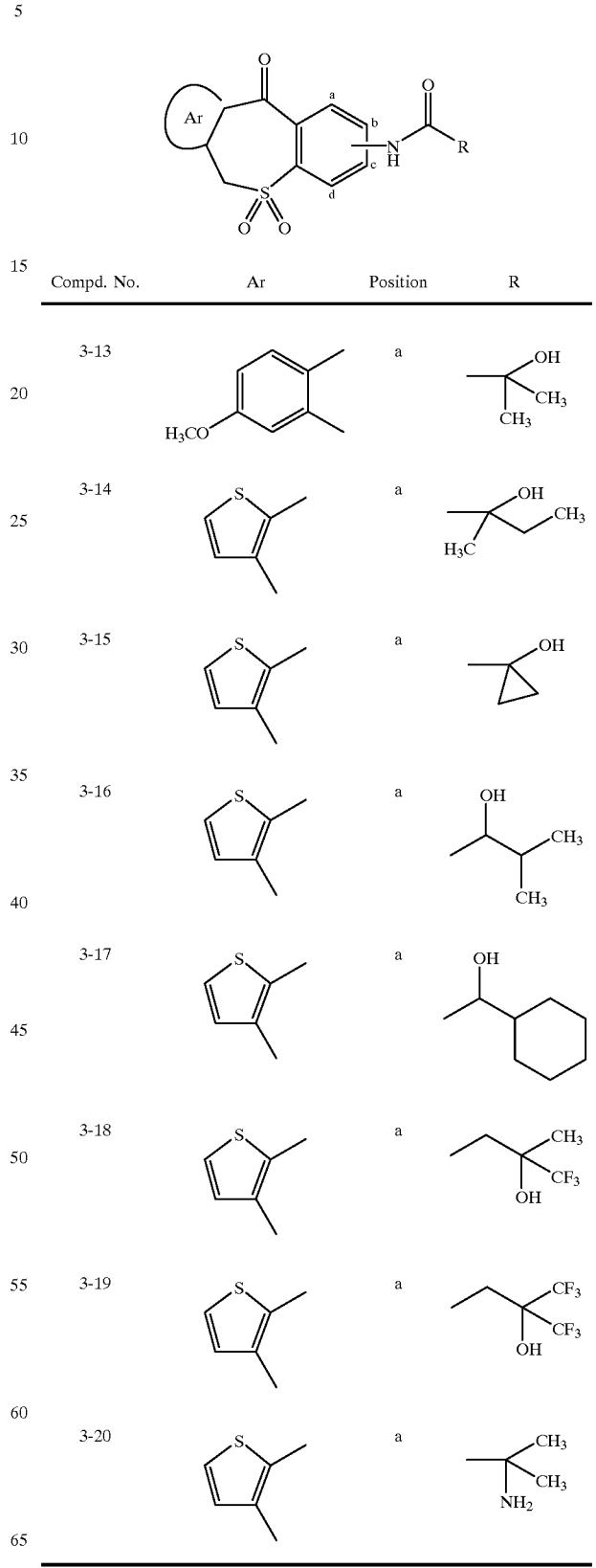

| Compd. No. | Ar | Position | R |
|---|---|---|---|
| 3-13 | 4-methoxy-2,3-dimethylphenyl | a | —C(OH)(CH₃)CH₃ |
| 3-14 | 2,3-dimethylthiophene | a | —C(OH)(CH₃)CH₂CH₃ |
| 3-15 | 2,3-dimethylthiophene | a | 1-hydroxycyclopropyl |
| 3-16 | 2,3-dimethylthiophene | a | —CH(OH)CH(CH₃)CH₃ |
| 3-17 | 2,3-dimethylthiophene | a | —CH(OH)cyclohexyl |
| 3-18 | 2,3-dimethylthiophene | a | —C(OH)(CH₂CH₃)CF₃ |
| 3-19 | 2,3-dimethylthiophene | a | —C(OH)(CF₃)CH₂CF₃ |
| 3-20 | 2,3-dimethylthiophene | a | —C(NH₂)(CH₃)CH₃ |

TABLE 3-2

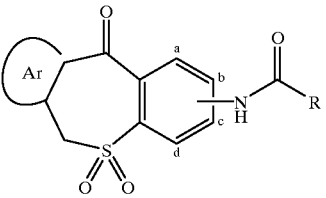

| Compd. No. | Ar | Position | R |
|---|---|---|---|
| 3-21 | 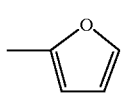 | a | 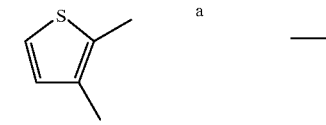 |
| 3-22 | 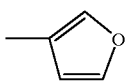 | a | 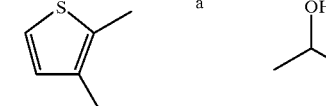 |
| 3-23 | 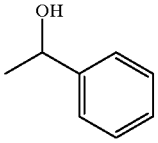 | a | 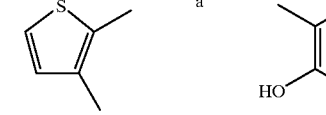 |
| 3-24 | 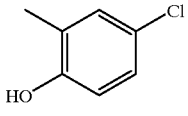 | a |  |
| 3-25 | 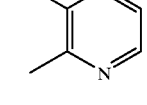 | a |  |
| 3-26 |  | a |  |
| 3-27 | 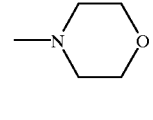 | a |  |
| 3-28 | 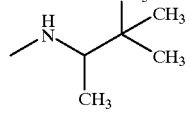 | a | 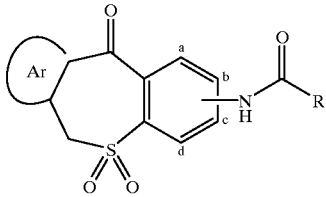 |

TABLE 3-2-continued

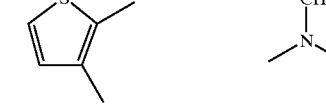

| Compd. No. | Ar | Position | R |
|---|---|---|---|
| 3-29 | 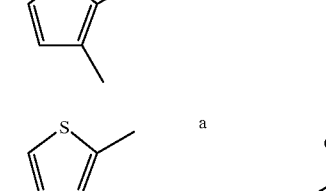 | a | 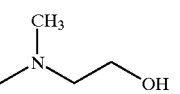 |
| 3-30 | 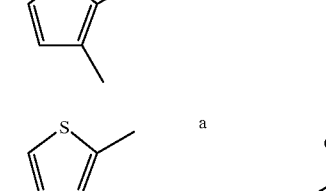 | a | 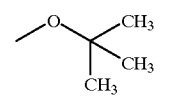 |
| 3-31 | 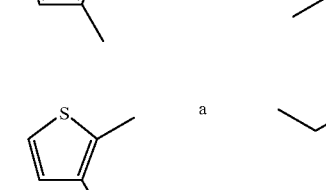 | a | 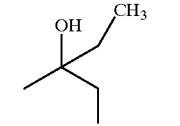 |
| 3-32 | 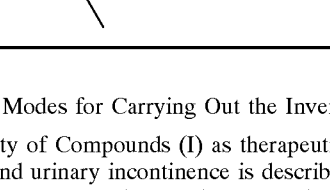 | a | 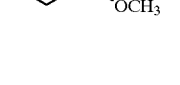 |

Best Modes for Carrying Out the Invention

The activity of Compounds (I) as therapeutic agents for pollakiuria and urinary incontinence is described below. In the following Test Examples 1 and 2, $IC_{50}$ value was defined as the concentration at which a test compound produces 50% relaxant of maximum response of detrusor muscle.

TEST EXAMPLE 1

Male albino Hartley guinea pigs (350–550 g) were used as test animals. Each animal was exsanguinated to death under sodium pentobarbital anesthesia. The lower abdominal cavity was opened and its bladder was positioned. The connective tissue and the fat tissue around the bladder were removed, and the bladder was washed. After bilateral pelvic nerves on the surface of the abdominal side of the bladder were dissected, the bladder was taken out on the entrance of ureter. The bladder was washed with a Krebs-Henseleit buffer [composition (mM): NaCl 118, KCl 4.7, $MgSO_4$ 1.2, $KH_2PO_4$ 1.2, $CaCl_2$ 2.5, $NaHCO_3$ 25, and D-glucose 11.1], and then put on a gauze patch soaked in the buffer in a Petri dish. The dome and the trigone of the bladder were cut away. The back of the bladder was cut vertically in the middle with scissors, and the bladder was put flat on the gauze patch. The mucosa of the bladder was removed. The back of the bladder was cut vertically to get 6 strips which are ca. 2.0 mm wide and ca. 10 mm long.

Each strip was tied at one end to plastic rod and placed in a 20 ml organ bath containing a Krebs-Henseleit solution which was maintained at 37° C. and bubbled vigorously with a gas mixture of 5% $CO_2$ and 95% $O_2$. The pH of the solution was adjusted to about 7.4. The other end of the strip was tied via silk thread to a force displacement transducer (NIHON KODEN TB-611T). The transducer was connected to a polygraph (NIHON KODEN AP-621G), and the changes in tension were recorded on a recorder (YOKOGAWA type 3066). The polygraph was graduated by 0.5 g/cm.

After the tissue was incubated in the buffer for 15 minutes without preloading, tension was added thereto for about one hour. The preloading tension added was 1.5 g and it was relaxed to about 1 g. The strips were allowed to equilibrate until their contractions became constant and tension was adjusted to 1 g. After this equilibrium period, 50 mmol/l KCl (the whole content in the bath) was added, and the tissue was washed 10 minutes later. KCl was added to the tissue at intervals of 30 minutes, followed by washing 10 minutes later, and KCl was applied repeatedly until the developed tension induced by KCl becomes constant. When the tissue was confirmed to contract constantly by the application of KCl and relax to the steady state after washing, 50 mmol/l KCl was applied again. After the tissue reached the steady state and the base line was obtained, a test compound was applied by the cumulative method (half-logarithmic increment). The contact time at each concentration was 30 minutes. The activity of the compound was expressed as the maximum relaxation rate (%) against the tension induced by the agonist.

The results are shown in Table 4.

In the following Test Example, KCl was used at a concentration different from that in Test Example 1.

TEST EXAMPLE 2

Isolated urinary bladder strips were prepared in the same manner as in Test Example 1, and the tension of the preparation was measured. After the tension of the tissue was adjusted to be a steady state at 1 g, 15 mmol/l KCl was applied. After the rhythmic contraction was confirmed to appear by KCl, the tissue was washed. Then, 15 mmol/l KCl was applied again. After the rhythmic contraction induced by KCl became constant, a test compound was applied by the cumulative method (half-logarithmic increment). The contact time at each concentration was 15–30 minutes. The activity of the compound was expressed as the maximum relaxation rate (%) against the tension induced by the agonist.

The results are shown in Table 4.

TABLE 4

| Compound No. | $IC_{50}$ ($\mu$M) KCl (15 mmol/l) | $IC_{50}$ ($\mu$M) KCl (50 mmol/l) |
|---|---|---|
| 1-1 | 2.6 | >10 |
| 1-2 | 5.1 | >10 |
| 1-3 | 6.3 | >10 |
| 1-4 | 3.2 | 4.5 |
| 1-5 | 4.0 | 8.7 |
| 1-7 | >10 | N.T. |
| 1-8 | 7.5 | N.T. |
| 1-9 | >10 | N.T. |
| 1-14 | >10 | N.T. |
| 1-19 | 4.3 | N.T. |
| 1-22 | 6.5 | N.T. |

TABLE 4-continued

| Compound No. | $IC_{50}$ ($\mu$M) KCl (15 mmol/l) | $IC_{50}$ ($\mu$M) KCl (50 mmol/l) |
|---|---|---|
| 1-24 | >10 | N.T. |
| 1-25 | 2.6 | 10.5 |
| 1-26 | 6.6 | 6.3 |
| 1-28 | >10 | N.T. |
| 1-29 | 2.4 | N.T. |
| 1-33 | 0.7 | N.T. |
| 1-35 | 2.5 | N.T. |
| 3-5 | 8.3 | 8.7 |
| 3-9 | >10 | N.T. |
| 3-12 | >10 | N.T. |
| 3-14 | >10 | N.T. |

N.T. = not tested

The effect of the compounds of the present invention can also be proved by the examination method described below which is used to evaluate the activity to prolong the intervals between micturitions.

TEST EXAMPLE 3

Male SD strain rats (200–300 g) were used as test animals. Each animal was anesthetized by intraperitoneally administering 50 mg/kg Nembutal. The hair on the abdomen, the thigh, and the back of the neck was shaved, followed by disinfection with 70% ethanol. The left femoral artery of the rat was exposed by incising the thigh for the insertion of a catheter into the femoral artery. A catheter filled with physiological saline containing heparin (1000 units/ml) was introduced approximately 2–3 cm into the artery so that its tip resided in the abdominal artery. The distal end of the catheter was exteriorized at the nape of the neck, sealed, and fixed on the skin tightly. A bladder catheter was implanted according to the method of Yaksh, et al., [Am. J. Physiol., vol.251, R1177–1185 (1986)]. The bladder was exposed through a midline abdominal incision. The bladder dome was given a small incision to make a small hole. A catheter filled with physiological saline was placed into the bladder and secured with a silk ligature. The other end of the catheter was exteriorized at the nape of the neck after being passed under the skin using a trocar. The exposed end of the catheter was sealed and fixed on the skin tightly. The abdominal muscles and skin were sutured, and the test animal was recovered from anesthesia.

The rat was weighed 24–48 hours after the operation. Each rat was placed in a Bollman cage (NATSUME SEISAKUSHO), and the test was done under partial restraint. The arterial catheter was connected to a pressure transducer (NIHON KODEN DX-300) used for the measurement of blood pressure. The bladder catheter was connected to a sylinge pump for physiological saline infusion and to a pressure transducer with PE50 tubing and a three-way stop-cock. Intravesical physiological saline infusion (0.05 ml/minute) was started and continued during the test. The changes of blood pressure, heart rate, and intravesical pressure were recorded with a polygraph (NIHON KODEN). The test animal was allowed to equilibration (for ca. 60–120 minutes) until its micturition pattern became constant. At this point, a basal value of each test parameter was recorded, and the rat was compulsorily given a test compound (in 0.3% carboxymethyl cellulose-physiological saline) at a dose of 1 mg/kg (body weight) by oral administration. The effects of the compound on the test parameters were observed for 5 hours after the administration. As a control compound, cromakalim was used. The contraction interval, the systemic blood pressure, and the heart rate were measured for 5 hours after the administration of the compound at one-hour intervals and were expressed as the relative values based on the pre-administration values which were regarded as 100.

The results are shown in Table 5 and Table 6.

TABLE 5

| Compound No. | Dose (mg/kg) | Time (h) | Contraction interval (%) |
|---|---|---|---|
| 1-1 | 1 | 0 | 100 ± 0 |
|  |  | 1 | 138 ± 15 |
|  |  | 2 | 166 ± 16 |
|  |  | 3 | 170 ± 6 |
|  |  | 4 | 181 ± 16 |
|  |  | 5 | 203 ± 21 |
| 1-2 | 1 | 0 | 100 ± 0 |
|  |  | 1 | 116 ± 8 |
|  |  | 2 | 136 ± 5 |
|  |  | 3 | 149 ± 9 |
|  |  | 4 | 143 ± 5 |
|  |  | 5 | 139 ± 6 |
| 1-3 | 1 | 0 | 100 ± 0 |
|  |  | 1 | 123 ± 15 |
|  |  | 2 | 135 ± 11 |
|  |  | 3 | 144 ± 10 |
|  |  | 4 | 160 ± 19 |
|  |  | 5 | 160 ± 16 |
| 1-7 | 1 | 0 | 100 ± 0 |
|  |  | 1 | 116 ± 9 |
|  |  | 2 | 138 ± 12 |
|  |  | 3 | 156 ± 17 |
|  |  | 4 | 155 ± 16 |
|  |  | 5 | 155 ± 17 |
| 1-9 | 1 | 0 | 100 ± 0 |
|  |  | 1 | 129 ± 23 |
|  |  | 2 | 123 ± 10 |
|  |  | 3 | 143 ± 12 |
|  |  | 4 | 135 ± 16 |
|  |  | 5 | 130 ± 5 |
| 1-19 | 1 | 0 | 100 ± 0 |
|  |  | 1 | 114 ± 9 |
|  |  | 2 | 139 ± 7 |
|  |  | 3 | 136 ± 11 |
|  |  | 4 | 145 ± 6 |
|  |  | 5 | 167 ± 15 |
| 1-24 | 1 | 0 | 100 ± 0 |
|  |  | 1 | 140 ± 11 |
|  |  | 2 | 121 ± 17 |
|  |  | 3 | 160 ± 19 |
|  |  | 4 | 169 ± 25 |
|  |  | 5 | 169 ± 25 |
| 1-25 | 0.1 | 0 | 100 ± 0 |
|  |  | 1 | 108 ± 9 |
|  |  | 2 | 140 ± 9 |
|  |  | 3 | 140 ± 12 |
|  |  | 4 | 148 ± 13 |
|  |  | 5 | 163 ± 17 |
| 1-26 | 0.1 | 0 | 100 ± 0 |
|  |  | 1 | 118 ± 8 |
|  |  | 2 | 137 ± 7 |
|  |  | 3 | 145 ± 7 |
|  |  | 4 | 152 ± 8 |
|  |  | 5 | 168 ± 7 |
| 1-28 | 1 | 0 | 100 ± 0 |
|  |  | 1 | 127 ± 10 |
|  |  | 2 | 139 ± 7 |
|  |  | 3 | 133 ± 6 |
|  |  | 4 | 140 ± 3 |
|  |  | 5 | 145 ± 3 |
| 1-33 | 1 | 0 | 100 ± 0 |
|  |  | 1 | 124 ± 15 |
|  |  | 2 | 137 ± 15 |
|  |  | 3 | 137 ± 4 |
|  |  | 4 | 142 ± 10 |
|  |  | 5 | 148 ± 21 |
| 1-35 | 1 | 0 | 100 ± 0 |
|  |  | 1 | 115 ± 2 |
|  |  | 2 | 133 ± 12 |
|  |  | 3 | 131 ± 15 |
|  |  | 4 | 152 ± 4 |
|  |  | 5 | 148 ± 3 |
| 3-5 | 1 | 0 | 100 ± 0 |
|  |  | 1 | 131 ± 12 |
|  |  | 2 | 152 ± 4 |
|  |  | 3 | 145 ± 18 |
|  |  | 4 | 157 ± 13 |
|  |  | 5 | 158 ± 4 |
| 3-9 | 1 | 0 | 100 ± 0 |
|  |  | 1 | 122 ± 7 |
|  |  | 2 | 128 ± 16 |
|  |  | 3 | 129 ± 18 |
|  |  | 4 | 150 ± 19 |
|  |  | 5 | 160 ± 21 |
| 3-12 | 1 | 0 | 100 ± 0 |
|  |  | 1 | 118 ± 18 |
|  |  | 2 | 153 ± 20 |
|  |  | 3 | 152 ± 17 |
|  |  | 4 | 161 ± 26 |
|  |  | 5 | 165 ± 19 |

TABLE 6

| Compound No. | Dose (mg/kg) | Time (h) | Contraction interval (%) | Blood pressure (%) | Heart rate (%) |
|---|---|---|---|---|---|
| 1-1 | 10 | 0 | 100 ± 0 | 100 ± 0 | 100 ± 0 |
|  |  | 1 | 124 ± 4 | 97 ± 5 | 97 ± 4 |
|  |  | 2 | 139 ± 9 | 96 ± 5 | 101 ± 4 |
|  |  | 3 | 154 ± 14 | 94 ± 4 | 100 ± 3 |
|  |  | 4 | 176 ± 13 | 94 ± 3 | 100 ± 3 |
|  |  | 5 | 190 ± 15 | 93 ± 3 | 100 ± 3 |
| 1-25 | 10 | 0 | 100 ± 0 | 100 ± 0 | 100 ± 0 |
|  |  | 1 | 133 ± 15 | 96 ± 3 | 111 ± 5 |
|  |  | 2 | 128 ± 10 | 93 ± 1 | 109 ± 5 |
|  |  | 3 | 149 ± 19 | 95 ± 2 | 110 ± 4 |
|  |  | 4 | 180 ± 22 | 93 ± 1 | 107 ± 6 |
|  |  | 5 | 183 ± 14 | 95 ± 1 | 104 ± 7 |
| 1-25 | 3 | 0 | 100 ± 0 | 100 ± 0 | 100 ± 0 |
|  |  | 1 | 129 ± 8 | 96 ± 1 | 105 ± 4 |
|  |  | 2 | 125 ± 14 | 94 ± 2 | 105 ± 4 |
|  |  | 3 | 143 ± 22 | 93 ± 2 | 104 ± 3 |
|  |  | 4 | 165 ± 22 | 93 ± 2 | 99 ± 2 |
|  |  | 5 | 161 ± 13 | 94 ± 2 | 98 ± 2 |
| Cromakalim | 1 | 0 | 100 | 100 | 100 |
|  |  | 1 | 124 | 46 | 98 |
|  |  | 2 | 133 | 52 | 100 |
|  |  | 3 | 142 | 54 | 98 |
|  |  | 4 | 133 | 60 | 99 |
|  |  | 5 | 133 | 64 | 99 |

Compound (I) can be prepared in generally employed pharmaceutical forms, such as tablets, capsules and syrups, and administered orally or parenterally through intramuscular injection, intravenous injection, drip infusion, or rectal administration in the form of suppositories. For preparing these pharmaceutical forms for oral or parenteral administration, generally known methods are applied. For example, the preparations may contain various excipients, lubricants, binders, disintegrating agents, isotonizing agents, emulsifiers, or the like.

Examples of the carriers which can be used are water, injectable distilled water, physiological saline, glucose, fructose, sucrose, mannitol, lactose, starch, cellulose, ethyl cellulose, sulfoxymethyl cellulose, hydroxypropyl cellulose, alginic acid, talc, sodium citrate, calcium carbonate, calcium hydrogenphosphate, magnesium stearate, urea, silicone resins, sorbitan fatty acid esters, and glycerin fatty acid esters.

The effective dose and the administration schedule of Compound (I) vary depending upon the mode of administration, the age and body weight of a patient, the type or degree of the symptom to be treated, etc., but generally, in the case of oral administration, Compound (I) is administered in a dose of 0.01 mg to 1 g/adult, preferably 0.05 to 50 mg/adult, once or several times per day. In the case of parenteral administration such as intravenous injection, Compound (I) is administered in a dose of 0.001 to 100 mg/adult, preferably 0.01 to 10 mg/adult, once or several times per day. It should be noted, however, that the dose may vary depending upon various conditions as stated above.

Certain embodiments of the invention are illustrated in the following Reference Examples and Examples.

The peak position of the proton nuclear magnetic resonance spectrum (NMR) used in Reference Examples and Examples is expressed in 1/1000000 unit (ppm) from tetramethylsilane toward a lower magnetic field. The peak form is expressed as follows:

s: singlet, d: doublet, t: triplet, q: quartet, m: multiplet, br: broad

REFERENCE EXAMPLE 1

Methyl 3-(3-aminophenylthiomethyl)thiophene-2-carboxylate

To a solution of 3-aminothiophenol (2.3 g, 18.7 mmol) and triethylamine (3.12 ml, 22.4 mmol) in dichloromethane (30 ml) was slowly added methyl 3-bromomethylthiophene-2-carboxylate (6.24 g, 22.4 mmol) under ice-cooling, followed by stirring for 30 minutes. After the reaction was completed, a saturated aqueous solution of sodium hydrogen carbonate was added to the reaction mixture. The organic layer was washed successively with a saturated aqueous solution of sodium hydrogen carbonate and a saturated aqueous solution of sodium chloride, and then dried over anhydrous magnesium sulfate. After the drying agent was filtered off, the organic layer was concentrated under reduced pressure. The obtained oily substance was purified by silica gel column chromatography (hexane/ethyl acetate= 7/1) to give oily methyl 3-(3-aminophenylthiomethyl) thiophene-2-carboxylate (4.82 g, 92%).

$^1$H-NMR (CDCl$_3$) δ: 3.63 (br, 2H), 3.84 (s, 3H), 4.52 (s, 2H), 6.49 (d, 1H, J=7.9 Hz), 6.64 (s, 1H), 6.71 (d, 1H, J=7.9 Hz), 7.02 (t, 1H, J=7.9 Hz), 7.05 (d, 1H, J=5.3 Hz), 7.37 (d, 1H, J=5.3 Hz)

REFERENCE EXAMPLE 2

Methyl 3-(3-acetamidophenylthiomethyl)thiophene-2-carboxylate

The amine obtained in Reference Example 1 (4.81 g, 17.3 mmol) was dissolved in dichloromethane (50 ml), and triethylamine (2.87 ml, 20.7 mmol) and acetic anhydride (1.78 ml, 19.0 mmol) were added thereto under ice-cooling, followed by stirring for 2 hours. After the reaction was completed, a saturated aqueous solution of sodium hydrogen carbonate was added to the reaction mixture. Then, the organic layer was washed successively with a saturated aqueous solution of sodium hydrogen carbonate and a saturated aqueous solution of sodium chloride, and then dried over anhydrous magnesium sulfate. After the drying agent was filtered off, the organic layer was concentrated under reduced pressure to give methyl 3-(3-acetamidophenylthiomethyl)thiophene-2-carboxylate (5.25 g, 95%).

$^1$H-NMR (CDCl$_3$) δ: 2.15 (s, 3H), 3.83 (s, 3H), 4.52 (s, 2H), 7.02 (d, 1H, J=7.8 Hz), 7.06 (d, 1H, J=5.1 Hz), 7.17 (t, 1H, J=7.8 Hz), 7.36 (d, 1H, J=5.1 Hz), 7.39 (d, 1H, J=7.8 Hz), 7.58 (br, 1H)

REFERENCE EXAMPLE 3

3-(3-Acetamidophenylthiomethyl)thiophene-2-carboxylic acid

The methyl ester obtained in Reference Example 2 (5.25 g, 17.2 mmol) was dissolved in methanol (30 ml), and a 2 mol/l aqueous solution of sodium hydroxide (30 ml) was added thereto, followed by stirring at 60° C. for one hour. Then, the reaction mixture was concentrated and adjusted to pH 3 with a 1 mol/l aqueous solution of hydrochloric acid. The precipitated white solid was separated by filtration, washed well with water, and then dried to give 3-(3-acetamidophenylthiomethyl)thiophene-2-carboxylic acid (4.06 g, 77%).

$^1$H-NMR (DMSO-d$_6$) δ: 2.03 (s, 3H), 4.54 (s, 2H), 6.96 (d, 1H, J=7.8 Hz), 7.11 (d, 1H, J=5.1 Hz), 7.19 (t, 1H, J=7.8 Hz), 7.37 (d, 1H, J=7.8 Hz), 7.63 (s, 1H), 7.67 (d, 1H, J=5.1 Hz), 9.93 (br, 1H)

REFERENCE EXAMPLE 4

9-Acetamido-4,10-dihydrothieno[3,2-c][1] benzothiepin-10-one [Compound A]

7-Acetamido-4,10-dihydrothieno[3,2-c][1] benzothiepin-10-one [Compound B]

The carboxylic acid obtained in Reference Example 3 (3.0 g, 9.9 mmol) was suspended in dichloromethane (30 ml), and trifluoroacetic anhydride (2.24 ml, 15.9 mmol) was added dropwise thereto under ice-cooling, followed by stirring at room temperature for 2 hours. After the reaction mixture was ice-cooled again, boron trifluoride diethyl etherate (0.5 equivalent) was added thereto, and the mixture was stirred overnight at room temperature. After the reaction was completed, the dichloromethane layer was washed successively with water, a 5% aqueous solution of sodium hydrogen carbonate and a saturated aqueous solution of sodium chloride, and then dried over anhydrous magnesium sulfate. The drying agent was filtered off, and the organic layer was concentrated under reduced pressure. The obtained oily substance was purified by silica gel column chromatography (chloroform/methanol=100/1) to give 9-acetamido-4,10-dihydrothieno[3,2-c][1]benzothiepin-10-one [Compound A] (0.74 g, 28%) and 7-acetamido-4,10-dihydrothieno[3,2-c][1]benzothiepin-10-one [Compound B] (1.03 g, 37%).

[Compound A] $^1$H-NMR (CDCl$_3$) δ: 2.18 (s, 3H), 3.95 (s, 2H), 6.96 (d, 1H, J=5.0 Hz), 7.39–7.45 (m, 2H), 7.60 (d, 1H, J=5.0 Hz), 8.28 (d, 1H, J=7.8 Hz), 9.98 (br, 1H)

[Compound B] $^1$H-NMR (DMSO-d$_6$) δ: 2.09 (s, 3H), 4.17 (s, 2H), 7.15 (d, 1H, J=5.3 Hz), 7.60 (d, 1H, J=8.9 Hz), 7.91 (d, 1H, J=5.3 Hz), 7.95 (s, 1H), 7.97 (d, 1H, J=8.9 Hz), 10.34 (br, 1H)

REFERENCE EXAMPLE 5

9-Amino-4,10-dihydrothieno[3,2-c][1]benzothiepin-10-one

In a mixed solvent of methanol (15 ml) and concentrated hydrochloric acid (15 ml), 9-acetamido-4,10-dihydrothieno

[3,2-c][1]benzothiepin-10-one obtained in Reference Example 4 (0.74 g, 2.5 mmol) was heated under reflux for one hour. The reaction mixture was poured into a saturated aqueous solution of sodium hydrogen carbonate, followed by extraction with ethyl acetate (25 ml). The organic layer was washed with a saturated aqueous solution of sodium chloride, and then dried over anhydrous magnesium sulfate. After the drying agent was filtered off, the organic layer was concentrated under reduced pressure to give 9-amino-4,10-dihydrothieno[3,2-c][1]benzothiepin-10-one as a yellow solid (0.6 g, 99%).

$^1$H-NMR (CDCl$_3$) δ: 3.92 (s, 2H), 5.70 (br, 1H), 6.63 (d, 1H, J=8.2 Hz), 6.92 (d, 1H, J=5.0 Hz), 6.95 (d, 1H, J=8.2 Hz), 7.10 (t, 1H, J=8.2 Hz), 7.51 (d, 1H, J=5.0 Hz)

REFERENCE EXAMPLE 6

7-Amino-4,10-dihydrothieno[3,2-c][1]benzothiepin-10-one

Substantially the same procedure as in Reference Example 5 was repeated using 7-acetamido-4,10-dihydrothieno[3,2-c][1]benzothiepin-10-one obtained in Reference Example 4 instead of 9-acetamido-4,10-dihydrothieno[3,2-c][1]benzothiepin-10-one to give 7-amino-4,10-dihydrothieno[3,2-c][1]benzothiepin-10-one as a white solid (yield: 94%).

$^1$H-NMR (CDCl$_3$) δ: 3.98 (s, 2H), 4.16 (br, 2H), 6.63 (d, 1H, J=8.6 Hz), 6.77 (s, 1H), 6.93 (d, 1H, J=5.0 Hz), 7.52 (d, 1H, J=5.0 Hz), 8.06 (d, 1H, J=8.6 Hz)

REFERENCE EXAMPLE 7

9-(3,3,3-Trifluoro-2-hydroxy-2-methylpropanoylamino)-4,10-dihydrothieno[3,2-c][1]benzothiepin-10-one In dimethylacetamide (10 ml) was dissolved 3,3,3-trifluoro-2-hydroxy-2-methylpropanoic acid (0.79 g, 5.0 mmol), and thionyl chloride (0.36 ml, 5.0 mmol) was added thereto at −15 C., followed by stirring at −15 to −5° C. for one hour. To the resulting mixture was added 9-amino-4,10-dihydrothieno[3,2-c][1]benzothiepin-10-one obtained in Reference Example 5 (0.62 g, 2.5 mmol), and the mixture was stirred overnight at room temperature. After the reaction mixture was concentrated under reduced pressure, the obtained oily residue was dissolved in ethyl acetate (50 ml). The organic layer was washed successively with a 5% aqueous solution of sodium hydrogen carbonate and a saturated aqueous solution of sodium chloride, and then dried over anhydrous magnesium sulfate. After the drying agent was filtered off, the organic layer was concentrated under reduced pressure. The obtained oily residue was purified by silica gel column chromatography (hexane/ethyl acetate=5/1), followed by trituration with hexane to give 9-(3,3,3-trifluoro-2-hydroxy-2-methylpropanoylamino)-4,10-dihydrothieno[3,2-c][1]benzothiepin-10-one (0.60 g, 63%).

$^1$H-NMR (DMSO-d$_6$) δ: 1.72 (s, 3H), 3.98 (s, 2H), 4.22 (br, 1H), 6.97 (d, 1H, J=5.0 Hz), 7.43 (t, 1H, J=8.0 Hz), 7.51 (d, 1H, J=8.0 Hz), 7.62 (d, 1H, J=5.0 Hz), 8.29 (d, 1H, J=8.0 Hz), 10.62 (br, 1H)

REFERENCE EXAMPLE 8

5-Acetamidophthalide

In tetrahydrofuran (100 ml) was dissolved 5-aminophthalide (10 g, 67.05 mmol), and triethylamine (18.64 ml, 134 mmol) was added thereto. To the resulting mixture was added dropwise acetic anhydride (12.61 ml, 134 mmol) under ice-cooling, followed by stirring at room temperature for 3 hours. After addition of a 5% aqueous solution of sodium hydrogen carbonate, the precipitated white solid was separated by filtration, washed several times with water, and then dried to give 5-acetamidophthalide (12.45 g, 97%).

$^1$H-NMR (DMSO-d$_6$) δ: 2.09 (s, 3H), 5.33 (s, 2H), 7.54 (d, 1H, J=8.2 Hz), 7.80 (d, 1H, J=8.2 Hz), 8.20 (s, 1H), 10.25 (br, 1H)

REFERENCE EXAMPLE 9

3-Acetamido-6-(4-methoxyphenoxymethyl)benzoic acid

4-Methoxyphenol (1.95 g, 15.7 mmol) was allowed to react with 28% sodium methoxide (15.7 mmol) in methanol (30 ml), at room temperature for 30 minutes. After the reaction was completed, the solvent was distilled off to obtain sodium phenoxide. The obtained sodium phenoxide and 5-acetamidophthalide obtained in Reference Example 8 (3.0 g, 15.7 mmol) were heated under reflux in xylene (30 ml) for 14 hours. The reaction mixture was poured into water and washed twice with ether (30 ml). The aqueous layer was adjusted to pH 3 with 1 mol/l hydrochloric acid and the precipitated solid was separated by filtration to give 3-acetamido-6-(4-methoxyphenoxymethyl)benzoic acid (2.49 g, 51%).

$^1$H-NMR (DMSO-d$_6$) δ: 2.06 (s, 3H), 3.70 (s, 3H), 5.30 (s, 2H), 6.83 (d, 2H, J=8.3 Hz), 6.86 (d, 2H, J=8.3 Hz), 7.52 (d, 1H, J=8.3 Hz), 7.77 (d, 1H, J=8.3 Hz), 8.17 (s, 1H), 10.10 (br, 1H), 12.96 (br, 1H)

REFERENCE EXAMPLE 10

9-Acetamido-2-methoxy-6,11-dihydrodibenz[b,e]oxepin-11-one

Substantially the same procedure as in Reference Example 4 was repeated using 3-acetamido-6-(4-methoxyphenoxymethyl)benzoic acid obtained in Reference Example 9 instead of 3-(3-acetamidophenylthiomethyl)thiophene-2-carboxylic acid to give 9-acetamido-2-methoxy-6,11-dihydrodibenz[b,e]oxepin-11-one (yield: 87%).

$^1$H-NMR (CDCl$_3$) δ: 2.20 (s, 3H), 3.85 (s, 3H), 5.11 (s, 2H), 6.98 (d, 1H, J=8.9 Hz), 7.10 (d, 1H, J=8.9 Hz), 7.32 (d, 1H, J=8.3 Hz), 7.61 (br, 1H), 7.66 (s, 1H), 8.09 (d, 1H, J=8.3 Hz)

REFERENCE EXAMPLE 11

9-Amino-2-methoxy-6,11-dihydrodibenz[b,e]oxepin-11-one

In a mixed solvent of concentrated hydrochloric acid (15 ml) and methanol (15 ml), 9-acetamido-2-methoxy-6,11-dihydrodibenz[b,e]oxepin-11-one obtained in Reference Example 10 (0.93 g, 3.1 mmol) was heated under reflux for one hour. After the reaction was completed, substantially the same procedure as in Reference Example 5 was repeated to give 9-amino-2-methoxy-6,11-dihydrodibenz[b,e]oxepin-11-one (yield: 74%).

$^1$H-NMR (CDCl$_3$) δ: 3.85 (s, 3H), 5.11 (s, 2H), 5.30 (br, 2H), 6.63 (d, 1H, J=8.9 Hz), 6.77 (s, 1H), 6.98 (d, 1H, J=8.9 Hz), 7.10 (d, 1H, J=8.9 Hz), 7.32 (d, 1H, J=8.9 Hz), 7.66 (s, 1H)

REFERENCE EXAMPLE 12

(S)-3,3,3-Trifluoro-2-hydroxy-2-methylpropionic acid

To a solution of 3,3,3-trifluoro-2-hydroxy-2-methylpropionic acid (13.0 g, 82.3 mmol) in ethanol (60 ml) was added dropwise (S)-(−)-1-phenethylamine (9.97 g, 82.3 mmol) at 0° C., followed by stirring at room temperature for one hour. Then, the resulting mixture was concentrated under reduced pressure to obtain a salt as white crystals. This salt was recrystallized from a 10% butanol/toluene solution (60 ml) six times to obtain a phenethylamine salt {(S,S) salt} of the S-form of 3,3,3-trifluoro-2-hydroxy-2-methylpropionic acid (3.85 g, 13.8 mmol, 97% e.e.) Optical purity was determined by $^1$H-NMR. The obtained {(S,S)} salt was dissolved in 2 mol/l hydrochloric acid and diethyl ether was added thereto, followed by stirring at room temperature for one hour. The organic layer was washed successively with water and a saturated aqueous solution of sodium chloride, and then dried over anhydrous sodium sulfate. After the drying agent was filtered off, the organic layer was concentrated under reduced pressure to give (S)-3,3,3-trifluoro-2-hydroxy-2-methylpropionic acid as white crystals (2.13 g, 13.5 mmol, recovery of S-form: 32%).

$^1$H-NMR (CDCl$_3$) δ: 1.65 (s, 3H)

REFERENCE EXAMPLE 13

(R)-3,3,3-Trifluoro-2-hydroxy-2-methylpropionic acid

Substantially the same procedure as in Reference Example 12 was repeated using (R)-(−)-1-phenethylamine instead of (S)-(−)-1-phenethylamine to give (R)-3,3,3-trifluoro-2-hydroxy-2-methylpropionic acid.

$^1$H-NMR (CDCl$_3$) δ: 1.65 (s, 3H)

REFERENCE EXAMPLE 14

(S)-9-(3,3,3-Trifluoro-2-hydroxy-2-methylpropanoylamino)-4,10-dihydrothieno[3,2-c][1]benzothiepin-10-one Substantially the same procedure as in Reference Example 7 was repeated using 9-amino-4,10-dihydrothieno[3,2-c][1]benzothiepin-10-one obtained in Reference Example 5 (0.56 g, 2.26 mmol) and (S)-3,3,3-trifluoro-2-hydroxy-2-methylpropanoic acid obtained in Reference Example 12 (0.72 g, 4.52 mmol) to give (S)-9-(3,3,3-trifluoro-2-hydroxy-2-methylpropanoylamino)-4,10-dihydrothieno[3,2-c][1]benzothiepin-10-one (0.87 g, 99%).

$^1$H-NMR (CDCl$_3$) δ: 1.72 (s, 3H), 3.98 (s, 2H), 4.16 (br, 1H), 6.98 (d, 1H, J=5.3 Hz), 7.43 (t, 1H, J=7.9 Hz), 7.52 (d, 1H, J=7.9 Hz), 7.62 (d, 1H, J=5.3 Hz), 8.28 (d, 1H, J=7.9 Hz), 10.72 (br, 1H)

REFERENCE EXAMPLE 15

(R)-9-(3,3,3-Trifluoro-2-hydroxy-2-methylpropanoylamino)-4,10-dihydrothieno[3,2-c][1]benzothiepin-10-one Substantially the same procedure as in Reference Example 7 was repeated using 9-amino-4,10-dihydrothieno[3,2-c][1]benzothiepin-10-one obtained in Reference Example 5 (0.37 g, 1.49 mmol) and (R)-3,3,3-trifluoro-2-hydroxy-2-methylpropanoic acid obtained in Reference Example 13 (0.47 g, 2.97 mmol) to give (R)-9-(3,3,3-trifluoro-2-hydroxy-2-ethylpropanoylamino)-4,10-dihydrothieno[3,2-][1]benzothiepin-10-one (0.57 g, 99%).

$^1$H-NMR (CDCl$_3$) δ: 1.72 (s, 3H), 3.98 (s, 2H), 4.16 (br, 1H), 6.97 (d, 1H, J=5.0 Hz), 7.43 (t, 1 H, J=7.9 Hz), 7.52 (d, 1H, J=7.9 Hz), 7.62 (d, 1H, J=5.0 Hz), 8.28 (d, 1H, J=7.9 Hz), 10.72 (br, 1H)

REFERENCE EXAMPLE 16

Methyl 2-(3-methoxyphenylthiomethyl)-6-nitrobenzoate

To a solution of 3-methoxythiophenol (0.54 g, 0.48 mmol) and triethylamine (0.43 ml, 0.59 mmol) in dichloromethane (30 ml) was slowly added methyl 2-bromomethyl-6-nitrobenzoate (1.45 g, 5.3 mmol) under ice-cooling, followed by stirring for 3 hours. After the reaction was completed, a saturated aqueous solution of sodium hydrogen carbonate was added to the reaction mixture. The organic layer was washed successively with a saturated aqueous solution of sodium hydrogen carbonate and a saturated aqueous solution of sodium chloride, and then dried over anhydrous magnesium sulfate. After the drying agent was filtered off, the organic layer was concentrated under reduced pressure. The obtained oily substance was purified by silica gel column chromatography (hexane/ethyl acetate= 7/1) to give methyl 2-(3-methoxyphenylthiomethyl)-6-nitrobenzoate (1.29 g, 99%).

$^1$H-NMR (CDCl$_3$) δ: 3.74 (s, 3H), 3.92 (s, 3H), 4.20 (s, 2H), 6.76 (ddd, 1H, J=7.9 Hz, 2.0 Hz, 1.0 Hz), 6.80 (t, 1H, J=2.0 Hz), 6.86 (ddd, 1H, J=7.9 Hz, 2.0 Hz, 1.0 Hz), 7.17 (t, 1H, J=7.9 Hz), 7.44 (d, 1H, J=7.9 Hz), 7.56 (dd, 1H, J=7.9 Hz, 1.0 Hz), 7.97 (dd, 1H, J=7.9 Hz, 1.0 Hz)

REFERENCE EXAMPLE 17

2-(3-Methoxyphenylthiomethyl)-6-nitrobenzoic acid

In methanol (10 ml) was dissolved methyl 2-(3-methoxyphenylthiomethyl)-6-nitrobenzoate obtained in Reference Example 16 (0.96 g, 2.88 mmol), and a 4 mol/l aqueous solution of sodium hydroxide (10 ml) was added thereto, followed by heating under reflux for 2 hours. After the reaction, the reaction mixture was concentrated and adjusted to pH 3 with a 1 mol/l aqueous solution of hydrochloric acid to give 2-(3-methoxyphenylthiomethyl)-6-nitrobenzoic acid as a precipitated white solid (0.85 g, 92%).

$^1$H-NMR (DMSO-d$_6$) δ: 3.71 (s, 3H), 4.38 (s, 2H), 6.75–6.80 (m, 1H), 6.85–6.92 (m, 2H), 7.20 (t, 1H, J=7.6 Hz), 7.59 (t, 1H, J=7.9 Hz), 7.75 (d, 1H, J=7.9 Hz), 7.97 (d, 1H, J=7.9 Hz), 14.01 (br, 1H)

REFERENCE EXAMPLE 18

3-Methoxy-10-nitro-6,11-dihydrodibenzo[b,e]thiepin-11-one

In methylene chloride (30 ml) was suspended 2-(3-methoxyphenylthiomethyl)-6-nitrobenzoic acid obtained in Reference Example 17 (0.92 g, 2.88 mmol), and trifluoroacetic anhydride (0.81 ml, 5.76 mmol) was added thereto, followed by stirring at room temperature for 2 hours. The reaction mixture was ice-cooled, and boron trifluoride etherate (0.13 ml, 1.06 mmol) was added thereto, followed by reaction for one hour. After the reaction was completed, a saturated aqueous solution of sodium hydrogen carbonate was added to the reaction mixture. The organic layer was washed successively with a saturated aqueous solution of sodium hydrogen carbonate and a saturated aqueous solution of sodium chloride, and then dried over anhydrous magnesium sulfate. After the drying agent was filtered off, the organic layer was concentrated under reduced pressure. The obtained oily substance was purified by silica gel column chromatography (hexane/ethyl acetate=6/1) to give 3-methoxy-10-nitro-6,11-dihydrodibenzo[b,e]thiepin-11-one (0.40 g, 46%).

$^1$H-NMR (CDCl$_3$) δ: 3.84 (s, 3H), 4.07 (s, 2H), 6.75 (d, 1H, J=2.3Hz), 6.91 (dd, 1H, J=8.9Hz, 2.0Hz), 7.50–7.54 (m, 2H), 7.92 (dd, 1H, J=5.9 Hz, 3.6 Hz), 7.98 (d, 1H, J=8.9 Hz)

EXAMPLE 1-1

5,5-Dioxo-9-(3,3,3-trifluoro-2-hydroxy-2-methylpropanoylamino)-4,10-dihydrothieno[3,2-c][1]benzothiepin-10-one (Compound 1-1)

In dichloromethane (30 ml) was dissolved 9-(3,3,3-trifluoro-2-hydroxy-2-methylpropanoylamino)-4,10-dihydrothieno[3,2-c][1]benzothiepin-10-one obtained in Reference Example 7 (0.3 g, 0.77 mmol), and 3-chloroperbenzoic acid (0.67 g, 3.5 equivalents) was added thereto under ice-cooling, followed by stirring at room temperature for 3 hours. After the reaction was completed, the reaction mixture was washed successively with a 5% aqueous solution of sodium sulfite, a 5% aqueous solution of sodium hydrogen carbonate and a saturated aqueous solution of sodium chloride, and then dried over anhydrous magnesium sulfate. After the drying agent was filtered off, the organic layer was concentrated under reduced pressure. The obtained oily residue was purified by silica gel column chromatography (hexane/ethyl acetate=3/1) and then triturated with isopropyl ether to give Compound 1-1 (0.21 g, 64%).

$^1$H-NMR (CDCl$_3$) δ: 1.74 (s, 3H), 4.68 (s, 2H), 7.03 (d, 1H, J=5.1 Hz), 7.74 (d, 1H, J=5.1 Hz), 7.76 (d, 1H, J=8.3 Hz), 7.97–8.03 (m, 2H), 8.67 (d, 1H, J=8.3 Hz), 10.80 (br, 1H)

In the following Examples 1-2 to 1-24, Examples 1-26 to 1-47, Examples 1-53 to 1-55, Examples 2-1 to 2-12 and Examples 3-1 to 3-32, substantially the same procedure as in Example 1-1 was repeated except that the corresponding tricyclic benzothiepine derivative was used instead of 9-(3,3,3-trifluoro-2-hydroxy-2-methylpropanoylamino)-4,10-dihydrothieno[3,2-c][1]benzothiepin-10-one to give the desired compound. In Examples 1-51, 1-52 and 2-10, substantially the same procedure as in Example 1-50 was repeated except that the corresponding tricyclic benzothiepine derivative was used instead of the starting material of Example 1-50, 3-methoxy-10-(3,3,3-trifluoro-2-hydroxy-2-methylpropanoylamino)-6,11-dihydrodibenzo[b,e]thiepin-11-one to give the desired compound.

EXAMPLE 1-2

5,5-Dioxo-7-(3,3,3-trifluoro-2-hydroxy-2-methylpropanoylamino)-4,10-dihydrothieno[3,2-c][1]benzothiepin-10-one (Compound 1-2) (yield: 68%)

$^1$H-NMR (DMSO-d$_6$) δ: 1.62 (s, 3H), 5.27 (s, 2H), 7.24 (d, 1H, J=5.0Hz), 7.57 (br, 1H), 8.03–8.09 (m, 2H), 8.26 (d, 1H, J=7.9 Hz), 8.73 (s, 1H), 10.81 (br, 1H)

EXAMPLE 1-3

5,5-Dioxo-1-(3,3,3-trifluoro-2-hydroxy-2-methylpropanoylamino)-6,11-dihydrodibenzo[b,e]thiepin-11-one (Compound 1-3) (yield: 90%)

$^1$H-NMR (CDCl$_3$) δ: 1.74 (s, 3H), 4.04 (br, 1H), 4.81 (s, 2H), 7.48–7.63 (m, 2H), 7.71 (t, 1H, J=8.1 Hz), 7.90 (d, 1H, J=8.1 Hz), 8.05 (d, 1H, J=8.1 Hz), 8.46 (d, 1H, J=8.1 Hz), 9.76 (br, 1H)

EXAMPLE 1-4

5,5-Dioxo-3-(3,3,3-trifluoro-2-hydroxy-2-methylpropanoylamino)-6,11-dihydrodibenzo[b,e]thiepin-11-one (Compound 1-4) (yield: 88%)

$^1$H-NMR (DMSO-d$_6$) δ: 1.62 (s, 3H), 5.28 (s, 2H), 7.50–7.66 (m, 3H), 7.91 (d, 1H, J=8.3 Hz), 7.96 (d, 1H, J=8.3 Hz), 8.22 (d, 1H, J=8.3 Hz), 8.65 (s, 1H), 10.69 (br, 1H)

EXAMPLE 1-5

9,9-Dioxo-5-(3,3,3-trifluoro-2-hydroxy-2-methylpropanoylamino)-4,10-dihydrothieno[2,3-c][1]benzothiepin-4-one (Compound 1-5) (yield: 70%)

$^1$H-NMR (DMSO-d$_6$) δ: 1.54 (s, 3H), 5.45 (s, 2H), 7.33 (d, 1H, J=5.3Hz), 7.59 (d, 1H, J=5.3 Hz), 7.72 (br, 1H), 7.82–7.88 (m, 2H), 8.15 (d, 1H, J=7.1 Hz), 10.61 (br, 1H)

EXAMPLE 1-6

9,9-Dioxo-7-(3,3,3-trifluoro-2-hydroxy-2-methylpropanoylamino)-4,10-dihydrothieno[2,3-c][1]benzothiepin-4-one (Compound 1-6) (yield: 72%)

$^1$H-NMR (DMSO-d$_6$) δ: 1.61 (s, 3H), 5.52 (s, 2H), 7.56–7.64 (m, 3H), 7.97 (d, 1H, J=8.3 Hz), 8.24 (d, 1H, J=8.3 Hz), 8.69 (s, 1H), 10.80 (br, 1H)

EXAMPLE 1-7

9,9-Dioxo-5-(3,3,3-trifluoro-2-hydroxy-2-methylpropanoylamino)-4,10-dihydrofuro[2,3-c][1]benzothiepin-4-one (Compound 1-7) (yield: 80%)

$^1$H-NMR (DMSO-d$_6$) δ: 1.58 (s. 3H), 5.38 (s, 2H), 6.83 (d, 1H, J=2.0 Hz), 7.79 (d, 1H, J=2.0 Hz), 7.83–7.93 (m, 2H), 8.42 (d, 1H, J=7.9 Hz), 10.88 (br, 1H)

EXAMPLE 1-8

9,9-Dioxo-7-(3,3,3-trifluoro-2-hydroxy-2-methylpropanoylamino)-4,10-dihydrofuro[2,3-c][1]benzothiepin-4-one (Compound 1-8) (yield: 73%)

$^1$H-NMR (DMSO-d$_6$) δ: 1.62 (s, 3H), 5.46 (s, 2H), 6.96 (d, 1H, J=2.0 Hz), 7.82 (d, 1H, J=2.0 Hz), 7.98 (d, 1H, J=8.3Hz), 8.27 (d, 1H, J=8.3Hz), 8.76 (s, 1H), 10.78 (br, 1H)

EXAMPLE 1-9

5,5-Dioxo-8-(3,3,3-trifluoro-2-hydroxy-2-methylpropanoylamino)-4,10-dihydrothieno[3,2-c][1]benzothiepin-10-one (Compound 1-9) (yield: 67%)

$^1$H-NMR (DMSO-d$_6$) δ: 1.61 (s, 3H), 5.20 (s, 2H), 7.24 (d, 1H, J=5.0 Hz), 7.55 (br, 1H), 8.03 (d, 1H, J=5.0 Hz), 8.29 (dd, 1H, J=8.6 Hz, 2.3 Hz), 8.51 (d, 1H, J=2.3 Hz), 10.67 (br, 1H)

EXAMPLE 1-10

5,5-Dioxo-6-(3,3,3-trifluoro-2-hydroxy-2-methylpropanoylamino)-4,10-dihydrothieno[3,2-c][1]benzothiepin-10one (Compound 1-10) (yield: 80%)

$^1$H-NMR (CDCl$_3$) δ: 1.57 (s, 3H), 3.93 (br, 1H), 4.83 (s, 2H), 7.00 (d, 1H, J=5.0 Hz), 7.66–7.79 (m, 3H), 8.91 (dd, 1H, J=8.6 Hz, 1.3 Hz), 11.41 (br, 1H)

EXAMPLE 1-11

5,5-Dioxo-9-(3,3,3-trifluoro-2-hydroxy-2-methylpropanoylamino)-4,10-dihydrofuro[3,2-c][1]benzothiepin-10one (Compound 1-11) (yield: 89%)

$^1$H-NMR (DMSO$_6$) δ: 1.57 (s, 3H), 5.11 (s, 2H), 6.79 (s, 1H), 7.79–7.97 (m, 3H), 8.14 (s, 1H), 8.50 (d, 1H, J=4.5 Hz), 11.11 (br, 1H)

EXAMPLE 1-12

5,5-Dioxo-8-(3,3,3-trifluoro-2-hydroxy-2-methylpropanoylamino)-4,10-dihydrofuro[3,2-c][1]benzothiepin-10one (Compound 1-12) (yield: 53%)

$^1$H-NMR (DMSO-d$_6$) δ: 1.61 (s, 3H), 5.07 (s, 2H), 6.80 (d, 1H, J=1.7 Hz), 7.54 (br, 1H), 8.05 (d, 1H, J=1.7 Hz), 8.12 (d, 1H, J=8.6 Hz), 8.29 (d, 1H, J=8.6 Hz), 8.53 (s, 1H), 10.67 (br, 1H)

EXAMPLE 1-13

5,5-Dioxo-6-(3,3,3-trifluoro-2-hydroxy-2-methylpropanoylamino)-4,10-dihydrofuro[3,2-c][1]benzothiepin-10one (Compound 1-13) (yield: 87%)

$^1$H-NMR (DMSO-d$_6$) δ: 1.63 (s, 3H), 5.02 (s, 2H), 6.78 (d, 1H, J=1.7 Hz), 7.46 (br, 1H), 8.02 (d, 1H, J=1.7 Hz), 8.28 (dd, 1H, J=8.4 Hz, 2.2 Hz), 8.76 (d, 1H, J=2.2 Hz), 10.72 (br, 1H

EXAMPLE 1-14

10,10-Dioxo-6-(3,3,3-trifluoro-2-hydroxy-2-methylpropanoylamino)-5,11-dihydro[1]benzothiepino[3,4-b]pyridin-5-one (Compound 1-14) (yield: 55%)

$^1$H-NMR (DMSO-d$_6$) δ: 1.51 (s, 3H), 5.38 (d, 1H, J=18.2 Hz), 5.45 (d, 1H, J=18.2 Hz), 7.55–7.67 (m, 2H), 7.75–7.93 (m, 3H), 8.10 (dd, 1H, J=7.9 Hz, 1.3 Hz), 8.78 (dd, 1H, J=4.6 Hz, 1.3 Hz), 10.60 (br, 1H)

EXAMPLE 1-15

10,10-Dioxo-7-(3,3,3-trifluoro-2-hydroxy-2-methylpropanoylamino)-5,11-dihydro[1]benzothiepino[3,4-b]pyridin-5-one (Compound 1-15) (yield: 40%)

$^1$H-NMR (CDCl$_3$) δ: 1.69 (s, 3H), 5.03 (s, 2H), 7.05 (s, 1H), 7.49 (dd, 1H, J=7.9 Hz, 4.6 Hz), 8.04–8.12 (m, 3H), 8.46 (dd, 1H, J=7.9 Hz, 1.6 Hz), 8.76 (dd, 1H, J=4.6 Hz, 1.6 Hz), 9.47 (br, 1H)

EXAMPLE 1-16

10,10-Dioxo-8-(3,3,3-trifluoro-2-hydroxy-2-methylpropanoylamino)-5,11-dihydro[1]benzothiepino[3,4-b]pyridin-5-one (Compound 1-16) (yield: 48%)

$^1$H-NMR (DMSO-d$_6$) δ: 1.61 (s, 3H), 5.47 (s, 2H), 7.58 (s, 1H), 7.63 (dd, 1H, J=7.9 Hz, 4.9 Hz), 7.98 (d, 1H, J=8.6 Hz), 8.24 (dd, 1H, J=8.6 Hz, 2.1Hz), 8.36 (dd, 1H, J=7.9 Hz, 1.6 Hz), 8.65 (d, 1H, J=2.1 Hz), 8.80 (dd, 1H, J=4.9 Hz, 1.6 Hz), 10.79 (br, 1H)

EXAMPLE 1-17

6,6-Dioxo-10-(3,3,3-trifluoro-2-hydroxy-2-methylpropanoylamino)-5,11-dihydro[1]benzothiepino[4,3-b]pyridin-11-one (Compound 1-17) (yield: 62%)

$^1$H-NMR (DMSO-d$_6$) δ: 1.60 (s, 3H), 5.44 (s, 2H), 7.73 (dd, 1H, J=7.9 Hz, 4.6 Hz), 7.85 (s, 1H), 7.86–7.96 (m, 3H), 8.24 (dd, 1H, J=6.6 Hz, 3.0 Hz), 8.81 (dd, 1H, J=4.6 Hz, 1.6 Hz), 10.40 (br, 1H)

EXAMPLE 1-18

10,10-Dioxo-6-(3,3,3-trifluoro-2-hydroxy-2-methylpropanoylamino)-5,11-dihydro[1]benzothiepino[3,4-c]pyridin-5-one (Compound 1-18) (yield: 39%)

$^1$H-NMR (CDCl$_3$) δ: 1.73 (s, 3H), 4.82 (s, 2H), 7.76 (t, 1H, J=8.1 Hz), 7.83 (d, 1H, J=5.1 Hz), 7.94 (dd, 1H, J=8.1 Hz, 1.0 Hz), 8.40 (dd, 1H, J=8.1 Hz, 1.0 Hz), 8.60 (s, 1H), 8.79 (d, 1H, J=5.1 Hz), 9.76 (br, 1H)

EXAMPLE 1-19

5,5-Dioxo-7-fluoro-1-(3,3,3-trifluoro-2-hydroxy-2-methylpropanoylamino)-6,11-dihydrodibenzo[b,e]thiepin-11-one (Compound 1-19) (yield: 89%)

$^1$H-NMR (DMSO-d$_6$) δ: 1.53 (s, 3H), 5.21 (s, 2H), 7.53–7.64 (m, 3H), 7.72 (br, 1H), 7.79–7.86 (m, 2H), 7.99 (d, 1H, J=8.6 Hz), 10.40 (br, 1H)

EXAMPLE 1-20

5,5-Dioxo-7-fluoro-3-(3,3,3-trifluoro-2-hydroxy-2-methylpropanoylamino)-6,11-dihydrodibenzo[b,e]thiepin-11-one (Compound 1-20) (yield: 88%)

$^1$H-NMR (DMSO-d$_6$) δ: 1.59 (s, 3H), 5.20 (s, 2H), 7.50–7.61 (m, 2H), 7.72 (d, 1H, J=8.3 Hz), 8.01 (d, 1H, J=8.3 Hz), 8.15 (d, 1H, J=8.3 Hz), 8.60 (s, 1H)

EXAMPLE 1-21

5,5-Dioxo-9-fluoro-1-(3,3,3-trifluoro-2-hydroxy-2-methylpropanoylamino)-6,11-dihydrodibenzo[b,e]thiepin-11-one (Compound 1-21) (yield: 100%)

$^1$H-NMR (DMSO-d$_6$) δ: 1.51 (s, 3H), 5.32 (s, 2H), 7.43–7.58 (m, 3H), 7.64 (br, 1H), 7.80–7.91 (m, 3H), 10.56 (br, 1H)

EXAMPLE 1-22

5,5-Dioxo-9-fluoro-3-(3,3,3-trifluoro-2-hydroxy-2-methylpropanoylamino)-6,11-dihydrodibenzo[b,e]thiepin-11-one (Compound 1-22) (yield: 72%)

$^1$H-NMR (DMSO-d$_6$) δ: 1.53 (s, 3H), 5.32 (s, 2H), 7.47–7.61 (m, 3H), 7.92 (d, 1H, J=8.7 Hz), 8.14 (dd, 1H, J=8.7 Hz, 2.3 Hz), 8.57 (d, 1H, J=2.3 Hz), 10.72 (br, 1H)

EXAMPLE 1-23

5,5-Dioxo-8-methyl-1-(3,3,3-trifluoro-2-hydroxy-2-methylpropanoylamino)-6,11-dihydrodibenzo[b,e]thiepin-11-one (Compound 1-23) (yield: 77%)

$^1$H-NMR (CDCl$_3$) δ: 1.73 (s, 3H), 2.41 (s, 3H), 3.90 (brs, 1H), 4.76 (s, 2H), 7.04 (s, 1H), 7.31 (d, 1H, J=8.3 Hz), 7.70 (t, 1H, J=7.9 Hz), 7.89 (d, 1H, J=7.9 Hz), 7.98 (d, 1H, J=8.3 Hz), 8.46 (d, 1H, J=7.9 Hz), 9.77 (br, 1H)

EXAMPLE 1-24

5,5-Dioxo-8-methoxy-1-(3,3,3-trifluoro-2-hydroxy-2-methylpropanoylamino)-6,11-dihydrodibenzo[b,e]thiepin-11-one (Compound 1-24) (yield: 46%)

$^1$H-NMR (CDCl$_3$) δ: 1.74 (s, 3H), 3.89 (s, 3H), 4.75 (s, 2H), 6.70 (d, 2H, J=2.3 Hz), 7.00 (dd, 1H, J=8.3 Hz, 2.3 Hz),

EXAMPLE 1-25

(S)-(+)-5,5-Dioxo-9-(3,3,3-trifluoro-2-hydroxy-2-methylpropanoylamino)-4,10-dihydrothieno[3,2-c][1]benzothiepin-10-one (Compound 1-25)

In dichloromethane (40 ml) was dissolved (S)-9-(3,3,3-trifluoro-2-hydroxy-2-methylpropanoylamino)-4,10-dihydrothieno[3,2-c][1]benzothiepin-10-one obtained in Reference Example 14 (1.07 g, 2.26 mmol), and 3-chloroperbenzoic acid (1.95 g, 3.5 equivalents) was added thereto under ice-cooling, followed by stirring at room temperature for 3 hours. After the reaction was completed, the reaction mixture was washed successively with a 5% aqueous solution of sodium sulfite, a 5% aqueous solution of sodium hydrogen carbonate and a saturated aqueous solution of sodium chloride, and then dried over anhydrous magnesium sulfate. After the drying agent was filtered off, the organic layer was concentrated under reduced pressure. The obtained oily residue was purified by silica gel column chromatography (hexane/ethyl acetate=3/1) and then triturated with isopropyl ether to give Compound 1-25 (0.71 g, 75%).

m.p. (melting point): 254–256° C.
$[\alpha]_D^{20}$ +32.2° (c=0.10, $CH_3OH$)
$^1$H-NMR (DMSO-$d_6$) δ: 1.57 (s, 3H), 5.21 (s, 2H), 7.19 (d, 1H, J=5.0Hz), 7.78 (br, 1H), 7.83–7.91 (m, 2H), 8.05 (d, 1H, J=5.0 Hz), 8.41 (d, 1H, J=7.2 Hz), 10.88 (br, 1H)

EXAMPLE 1-26

(R)-(−)-5,5-Dioxo-9-(3,3,3-trifluoro-2-hydroxy-2-methylpropanoylamino)-4,10-dihydrothieno [3,2-c][1]benzothipin-10-one (Compound 1-26) (yield: 76%)

m.p. (melting point): 254–256° C.
$[\alpha]_D^{20}$ −38.2° (c=0.10, $CH_3OH$)
$^1$H-NMR (DMSO-$d_6$) δ: 1.56 (s, 3H), 5.23 (s, 2H), 7.18 (d, 1H, J=5.1 Hz), 7.79 (br, 1H), 7.83–7.91 (m, 2H), 8.07 (d, 7 H, J=5.1 Hz), 8.39 (d, 1H, J=7.0 Hz), 10.87 (br, 1H)

EXAMPLE 1-27

5,5-Dioxo-8-hydroxy-1-(3,3,3-trifluoro-2-hydroxy-2-methylpropanoylamino)-6,11-dihydrobenzo[b,e]thiepin-11-one (Compound 1-27) (yield: 36%)

$^1$H-NMR (DMSO-$d_6$) δ: 1.54 (s, 3H), 5.20 (s, 2H), 6.76 (d, 1H, J=2.0 Hz), 6.91 (dd, 1H, J=8.6 Hz, 2.0 Hz), 7.77–7.83 (m, 4H), 8.19 (dd, 1H, J=5.6 Hz, 3.3 Hz), 10.25 (brs, 1H)

EXAMPLE 1-28

5,5-Dioxo-6-methoxy-9-(3,3,3-trifluoro-2-hydroxy-2-methylpropanoylamino)-4,10-dihydrothieno[3,2-c][1]benzothiepin-10-one (Compound 1-28) (yield: 79%)

$^1$H-NMR (DMSO-$d_6$) δ: 1.55 (s, 3H), 3.94 (s, 3H), 5.13 (s, 2H), 7.11 (d, 1H, J=5.0 Hz), 7.50 (d, 1H, J=9.2Hz), 7.68 (br, 1H), 7.95 (d, 1H, J=5.0 Hz), 8.17 (d, 1H, J=9.2 Hz), 10.18 (br, 1H)

EXAMPLE 1-29

5,5-Dioxo-6-methyl-9-(3,3,3-trifluoro-2-hydroxy-2-methylpropanoylamino)-4,10 -dihydrothieno[3,2-c][1]benzothiepin-10-one (Compound 1-29) (yield: 88%)

$^1$H-NMR (DMSO-$d_6$) δ: 1.56 (s, 3H), 2.73 (s, 3H), 5.21 (s, 2H), 7.12 (d, 1H, J=5.1 Hz), 7.59 (d, 1H, J=8.6 Hz), 7.75 (br, 1H), 7.97 (d, 1H, J=5.1 Hz), 8.20 (d, 1H, J=8.6 Hz), 10.37 (br, 1H)

7.70 (t, 1H, J=7.9 Hz), 7.90 (d, 1H, J=7.9 Hz), 8.12 (d, 1H, J=8.9 Hz), 8.47 (d, 1H, J=7.9 Hz), 9.82 (br, 1H)

EXAMPLE 1-30

8-Chloro-5,5-dioxo-7-(3,3,3-trifluoro-2-hydroxy-2-methylpropanoylamino)-4,10-dihydrothieno[3,2-c][1]benzothiepin-10-one (Compound 1-30) (yield: 65%)

$^1$H-NMR (CDCl$_3$) δ: 1.81 (s, 3H), 3.75 (br, 1H), 4.73 (s, 2H), 7.06 (d, 1H, J=5.0 Hz), 7.76 (d, 1H, J=5.0 Hz), 8.23 (s, 1H), 9.31 (s, 1H), 9.46 (br, 1H)

EXAMPLE 1-31

5,5-Dioxo-8-methyl-9-(3,3,3-trifluoro-2-hydroxy-2-methylpropanoylamino)-4,10-dihydrothieno[3,2-c][1]benzothiepin-10-one (Compound 1-31) (yield: 84%)

$^1$H-NMR (DMSO-$d_6$) δ: 1.55 (s, 3H), 2.34 (s, 3H), 4.99 (d, 1H, J=17.8 Hz), 5.08 (d, 1H, J=17.8 Hz), 7.12 (d, 1H, J=5.1 Hz), 7.38 (br, 1H), 7.70 (d, 1H, J=7.9 Hz), 7.89 (d, 1H, J=5.1 Hz), 7.90 (d, 1H, J=7.9 Hz), 9.92 (br, 1H)

EXAMPLE 1-32

5,5-Dioxo-8-methyl-7-(3,3,3-trifluoro-2-hydroxy-2-methylpropanoylamino)-4,10-dihydrothieno[3,2-c][1]benzothiepin-10-one (Compound 1-32) (yield: 96%)

$^1$H-NMR (DMSO-$d_6$) δ: 1.64 (s, 3H), 2.09 (s, 3H), 5.21 (s, 2H), 7.23 (d, 1H, J=5.0 Hz), 7.71 (br, 1H), 7.97 (s, 1H), 8.04 (d, 1H, J=5.0 Hz), 8.43 (s, 1H), 9.89 (br, 1H)

EXAMPLE 1-33

6-Chloro-5,5-dioxo-9-(3,3,3-trifluoro-2-hydroxy-2-methylpropanoylamino)-4,10-dihydrothieno[3,2-c][1]benzothiepin-10-one (Compound 1-33) (yield: 90%)

$^1$H-NMR (DMSO-$d_6$) δ: 1.55 (s, 3H), 5.30 (s, 2H), 7.14 (d, 1H, J=5.0 Hz), 7.80 (br, 1H), 7.82 (d, 1H, J=8.9 Hz), 8.00 (d, 1H, J=5.0 Hz), 8.28 (d, 1H, J=8.9 Hz), 10.43 (br, 1H)

EXAMPLE 1-34

5,5-Dioxo-8-methoxy-7-(3,3,3-trifluoro-2-hydroxy-2-methylpropanoylamino)-4,10-dihydrothieno[3,2-c]benzothiepin-10-one (Compound 1-34) (yield: 26%)

$^1$H-NMR (DMSO-$d_6$) δ: 1.63 (s, 3H), 4.08 (s, 3H), 5.27 (s, 2H), 7.25 (d, 1H, J=5.3 Hz), 7.68 (br, 1H), 8.08 (s, 1H), 8.12 (d, 1H, J=5.3 Hz), 9.02 (s, 1H), 9.78 (br, 1H)

EXAMPLE 1-35

5,5-Dioxo-6-fluoro-9-(3,3,3-trifluoro-2-hydroxy-2-methylpropanoylamino)-4,10-dihydrothieno[3,2-c][1]benzothiepin-10-one (Compound 1-35) (yield: 76%)

$^1$H-NMR (DMSO-$d_6$) δ: 1.58 (s, 3H), 5.25 (s, 2H), 7.15 (d, 1H, J=5.2 Hz), 7.57 (t, 1H, J=9.6 Hz), 7.67 (br, 1H), 7.93 (d, 1H, J=5.1 Hz), 8.37 (dd, 1H, J=9.6 Hz, 4.3 Hz), 10.50 (br, 1H)

EXAMPLE 1-36

8-Amino-6,5-dioxo-9-(3,3,3-trifluoro-2-hydroxy-2-methylpropanoylamino)-6,11-dihydrodibenzo[b,e]thiepin-11-one (Compound 1-36) (yield: 75%)

$^1$H-NMR (DMSO-$d_6$) δ: 1.55 (s, 3H), 5.00–5.15 (m, 2H), 6.35–6.45 (m, 3H) , 6.63 (dd, 1H, J=8.6 Hz, 2.0 Hz), 7.70–7.83 (m, 4H), 8.33 (dd, 1H, J=6.6 Hz, 3.3Hz), 10.29 (br, 1H)

EXAMPLE 1-37

8-Ethylamino-5,5-dioxo-1-(3,3,3-trifluoro-2-hydroxy-2-methylpropanoylamino)-6,11-dihydrodibenzo[b,e]thiepin-11-one (Compound 1-37) (yield: 25%)

$^1$H-NMR (CDCl$_3$) δ: 1.29 (t, 3H, J=7.3 Hz), 1.72 (s, 3H), 3.25 (q, 2H, J=7.3 Hz), 4.21 (br, 1H), 4.67 (s, 1H), 6.35 (d, 1H, J=2.0 Hz), 6.67 (dd, 1H, J=8.9 Hz, 2.0 Hz), 7.65 (t, 1H, J=8.2 Hz), 7.87 (dd, 1H, J=8.2 Hz, 1.0 Hz), 8.04 (d, 1H, J=8.9 Hz), 8.46 (dd, 1H, J=8.2 Hz, 1.0 Hz), 10.03 (br, 1H)

EXAMPLE 1-38

8-Acetylamino-5,5-dioxo-1-(3,3,3-trifluoro-2-hydroxy-2-methylpropanoylamino)-6,11-dihydrodibenzo[b,e]thiepin-11-one (Compound 1-38) (yield: 62%)

$^1$H-NMR (DMSO-d$_6$) δ: 1.54 (s, 3H), 2.09 (s, 3H), 5.29 (s, 2H), 7.57 (d, 1H, J=2.0 Hz), 7.76–7.90 (m, 5H), 8.05–8.15 (m, 1H), 10.30 (br, 1H), 10.39 (br, 1H)

EXAMPLE 1-39

8-(2,2-Dimethylpropanoylamino)-5,5-dioxo-1-(3,3,3-trifluoro-2-hydroxy-2-methylpropanoylamino)-6,11-dihydrodibenzo[b,e]thiepin-11-one (Compound 1-39) (yield: 98%)

$^1$H-NMR (CDCl$_3$) δ: 1.32 (s, 9H), 1.72 (s, 3H), 4.75 (s, 2H), 7.39 (dd, 1H, J=8.6 Hz, 2.0 Hz), 7.57 (br, 1H), 7.69 (t, 1H, J=8.3 Hz), 7.76 (s, 1H), 7.89 (d, 1H, J=8.3 Hz), 8.02 (d, 1H, J=8.6 Hz), 8.45 (d, 1H, J=8.3 Hz), 9.82 (br, 1H)

EXAMPLE 1-40

5,5-Dioxo-7-methoxy-1-(3,3,3-trifluoro-2-hydroxy-2-methylpropanoylamino)-6,11-dihydrodibenzo[b,e]thiepin-11-one (Compound 1-40) (yield: 99%)

$^1$H-NMR (CDCl$_3$) δ: 1.72 (s, 3H), 3.89 (s, 3H), 4.03 (br, 1H), 4.72 (s, 2H), 7.13 (d, 1H, J=8.3 Hz), 7.45 (t, 1H, J=8.3 Hz), 7.57 (d, 1H, J=8.3 Hz), 7.68 (t, 1H, J=8.3 Hz), 7.88 (d, 1H, J=8.3 Hz), 8.46 (d, 1H, J=8.3 Hz), 9.69 (br, 1H)

EXAMPLE 1-41

5,5-Dioxo-7-methoxy-3-(3,3,3-trifluoro-2-hydroxy-2-methylpropanoylamino)-6,11-dihydrodibenzo[b,e]thiepin-11-one (Compound 1-41) (yield: 88%)

$^1$H-NMR (CDCl$_3$) δ: 1.72 (s, 3H), 3.90 (s, 3H), 4.89 (s, 2H), 7.11 (dd, 1H, J=8.3 Hz, 1.6 Hz), 7.39–7.50 (m, 2H), 7.90 (d, 1H, J=8.3 Hz), 8.11 (dd, 1H, J=8.3 Hz, 1.6 Hz), 8.20 (d, 1H, J=1.6 Hz), 9.27 (br, 1H)

EXAMPLE 1-42

5,5-Dioxo-7-isopropyloxy-1-(3,3,3-trifluoro-2-hydroxy-2-methylpropanoylamino)-6,11-dihydrodibenzo[b,e]thiepin-11-one (Compound 1-42) (yield: 96%)

$^1$H-NMR (CDCl$_3$) δ: 1.36 (d, 6H, J=6.0 Hz), 1.72 (s, 3H), 4.16 (br, 1H), 4.71 (s, 2H), 7.11 (d, 1H, J=8.1 Hz), 7.42 (t, 1H, J=8.1 Hz), 7.54 (d, 1H, J=8.1 Hz), 7.68 (t, 1H, J=8.1 Hz), 7.87 (d, 1H, J=8.1 Hz), 8.46 (d, 1H, J=8.1 Hz), 9.69 (br, 1H)

EXAMPLE 1-43

5,5-Dioxo-7-isopropyloxy-3-(3,3,3-trifluoro-2-hydroxy-2-methylpropanoylamino)-6,11-dihydrodibenzo[b,e]thiepin-11-one (Compound 1-43) (yield: 92%)

$^1$H-NMR (CDCl$_3$) δ: 1.36 (d, 6H, J=6.3 Hz), 1.70 (s, 3H), 4.59–4.67 (m, 1H), 4.88 (s, 2H), 7.11 (d, 1H, J=8.3 Hz), 7.37–7.48 (m, 2H), 7.86 (d, 1H, J=8.3 Hz), 8.05 (dd, 1H, J=8.3, 2.0 Hz), 8.22 (d, 1H, J=2.0 Hz), 9.28 (br, 1H)

EXAMPLE 1-44

5,5-Dioxo-10-methoxy-3-(3,3,3-trifluoro-2-hydroxy-2-methylpropanoylamino)-6,11-dihydrodibenzo[b,e]thiepin-11-one (Compound 1-44) (yield: 75%)

$^1$H-NMR (DMSO-d$_6$) δ: 1.61 (s, 3H), 3.78 (s, 3H), 5.08 (s, 2H), 7.08 (d, 1H, J=7.9 Hz), 7.13 (d, 1H, J=7.9 Hz), 7.45–7.50 (m, 2H), 7.78 (d, 1H, J=7.9 Hz), 8.18 (d, 1H, J=7.9 Hz), 8.58 (s, 1H), 10.62 (br, 1H)

EXAMPLE 1-45

8,10-Dimethoxy-5,5-dioxo-1-(3,3,3-trifluoro-2-hydroxy-2-methylpropanoylamino)-6,11-dihydrobenzo[b,e]thiepin-11-one (Compound 1-45) (yield: 53%)

$^1$H-NMR (CDCl$_3$) δ: 1.74 (s, 3H), 3.74 (s, 3H), 3.84 (s, 3H), 4.61 (d, 1H, J=15.8 Hz), 4.75 (d, 1H, J=15.8 Hz), 6.44 (d, 1H, J=5.3 Hz), 6.45 (d, 1H, J=5.3 Hz), 7.69 (t, 1H, J=7.9 Hz), 7.80 (dd, 1H, J=7.9 Hz, 1.0 Hz), 8.68 (dd, 1H, J=7.9 Hz, 1.0 Hz), 10.50 (br, 1H)

EXAMPLE 1-46

(S)-5,5-Dioxo-2-nitro-9-(3,3,3-trifluoro-2-hydroxy-2-methylpropanoylamino)-4,10-dihydrothieno[3,2-c][1]benzothiepin-10-one (Compound 1-46) (yield: 35%)

$^1$H-NMR (DMSO-d$_6$) δ: 1.52 (s, 3H), 5.34 (s, 2H), 7.66 (s, 1H), 7.88–7.96 (m, 2H), 7.97–8.04 (m, 1H), 8.08 (s, 1H), 10.90 (br, 1H)

EXAMPLE 1-47

(S)-5,5-Dioxo-3-nitro-9-(3,3,3-trifluoro-2-hydroxy-2-methylpropanoylamino)-4,10-dihydrothieno[3,2-c][1]benzothiepin-10-one (Compound 1-47) (yield: 43%)

$^1$H-NMR (DMSO-d$_6$) δ: 1.52 (s, 3H), 5.43 (s, 2H), 7.68 (s, 1H), 7.83–7.94 (m, 2H), 7.99–8.07 (m, 1H), 9.16 (s, 1H), 10.79 (br, 1H)

EXAMPLE 1-48

2-Methoxy-9-(3,3,3-trifluoro-2-hydroxy-2-methylpropanoylamino)-6,11-dihydrodibenz[b,e]oxepin-11-one (Compound 1-48)

In dimethylacetamide (8 ml) was dissolved 3,3,3-trifluoro-2-hydroxy-2-methylpropanoic acid (0.73 g, 4.63 mmol), and thionyl chloride (0.36 ml, 4.63 mmol) was added thereto at −15° C., followed by stirring at −15 to −5° C. for one hour. To the reaction mixture was added 9-amino-2-methoxy-6,11-dihydrodibenz[b,e]oxepin-11-one obtained in Reference Example 11 (0.59 g, 2.32 mmol), and the mixture was stirred overnight at room temperature. The reaction mixture was concentrated under reduced pressure, and the obtained oily residue was dissolved in ethyl acetate (25 ml). The organic layer was washed successively with a 5% aqueous solution of sodium hydrogen carbonate and a saturated aqueous solution of sodium chloride, and then dried over anhydrous magnesium sulfate. After the drying agent was filtered off, the organic layer was concentrated under reduced pressure. The obtained oily substance was purified by silica gel column chromatography (hexane/ethyl acetate=3/1), followed by trituration with isopropyl ether to give Compound 1-48 (yield: 87%).

$^1$H-NMR (CDCl$_3$) δ: 1.75 (s, 3H), 3.84 (s, 3H), 4.17 (br, 1H), 5.13 (s, 2H), 6.98 (d, 1H, J=8.9 Hz), 7.11 (d, 1H, J=8.9 Hz), 7.37 (d, 1H, J=7.9 Hz), 7.65 (s, 1H), 7.82 (s, 1H), 8.09 (d, 1H, J=7.9 Hz), 8.61 (br, 1H)

EXAMPLE 1-49

3-Methoxy-10-(3,3,3-trifluoro-2-hydroxy-2-methylpropanoylamino)-6,11-dihydrodibenzo[b,e]thiepin-11-one (Compound 1-49)

In a mixture of water and ethanol (20 ml), 3-methoxy-10-nitro-6,11-dihydrodibenzo[b,e]thiepin-11-one obtained in Reference Example 18 (0.36 g, 1.2 mmol) was heated under reflux in the presence of reduced iron (0.36 g) and iron (III) chloride (40 mg) for 2 hours. After the reaction was completed, the reaction mixture was filtered while hot and the filtrate was evaporated under reduced pressure to give crude 10-amino-3-methoxy-6,11-dihydrodibenzo[b,e]thiepin-11-one (1.2 mmol). This crude product was added without purification to an acid chloride prepared from 3,3,3-trifluoro-2-hydroxy-2-methylpropanoic acid (0.38 g, 2.39 mmol) and thionyl chloride (0.36 ml, 2.39 mmol) in dimethylacetamide (10 ml) in the same manner as in Example 1-48, followed by stirring at room temperature for 6 hours. After the reaction, purification of the reaction product was carried out according to the procedure of Example 1-48 to give Compound 1-49 (0.32 g, yield: 65%).

$^1$H-NMR (CDCl$_3$) δ: 1.69 (s, 3H), 3.84 (s, 3H), 3.97 (d, 1H, J=14.2 Hz), 4.04 (d, 1H, J=14.2 Hz), 4.23 (br, 1H), 6.77 (d, 1H, J=2.3 Hz), 6.81 (dd, 1H, J=8.9, 2.3 Hz), 7.08 (dd, 1H, J=7.9, 0.7 Hz), 7.46 (t, 1H, J=7.9 Hz), 8.16 (dd, 1H, J=7.9, 0.7 Hz), 8.18 (d, 1H, J=8.9Hz), 9.76 (br, 1H)

EXAMPLE 1-50

5,5-Dioxo-3-methoxy-10-(3,3,3-trifluoro-2-hydroxy-2-methylpropanoylamino)-6,11-dihydrodibenzo[b,e]thiepin-11-one (Compound 1-50)

The same procedure as in Example 1-1 was repeated using 3-methoxy-10-(3,3,3-trifluoro-2-hydroxy-2-methylpropanoylamino)-6,11-dihydrodibenzo[b,e]thiepin-11-one obtained in Example 1-49 (0.28 g, 0.68 mmol) to give Compound 1-50 (0.32 g, yield: 99%).

$^1$H-NMR (DMSO-d$_6$) δ: 1.52 (s, 3H), 3.94 (s, 3H), 5.33 (s, 2H), 7.33–7.45 (m, 3H), 7.58 (t, 1H, J=8.1 Hz), 7.61 (s, 1H), 7.75 (d, 1H, J=8.1 Hz), 7.84 (d, 1H, J=8.6 Hz), 10.25 (br, 1H)

EXAMPLE 1-51

5,5-Dioxo-9-(3,3,3-trifluoro-2-hydroxy-2-methylpropanoylamino)-6,11-dihydrodibenzo[b,e]thiepin-11-one (Compound 1-51) (yield: 61%)

$^1$H-NMR (DMSO-d$_6$) δ: 1.58 (s, 3H), 5.31 (s, 2H), 7.44 (d, 1H, J=8.6 Hz), 7.48 (s, 1H), 7.82–8.01 (m, 5H), 8.39 (d, 1H, J=2.3 Hz), 10.31 (br, 1H)

EXAMPLE 1-52

5,5-Dioxo-7-(3,3,3-trifluoro-2-hydroxy-2-methylpropanoylamino)-6,11-dihydrodibenzo[b,e]thiepin-11-one (Compound 1-52) (yield: 61%)

$^1$H-NMR (CDCl$_3$) δ: 1.73 (s, 3H), 4.04 (br, 1H), 4.77 (s, 2H), 7.23 (d, 1H, J=8.2 Hz), 7.58 (t, 1H, J=8.2 Hz), 7.73 (dt, 1H, J=7.6 Hz, 1.3 Hz), 7.81 (dt, 1H, J=7.6 Hz, 1.6 Hz), 7.87 (dd, 1H, J=7.6 Hz, 1.6 Hz), 8.07 (dd, 1H, J=7.6 Hz, 1.3 Hz), 8.29 (d, 1H, J=8.2 Hz), 9.93 (br, 1H)

EXAMPLE 1-53

8-(3,3,3-Trifluoro-2-hydroxy-2-methylpropanoylamino)-1,10,10-trioxo-5,11-dihydro[1]benzothiepino[3,4-b]pyridin-5-one (Compound 1-53) (yield: 18%)

$^1$H-NMR (DMSO-d$_6$) δ: 1.60 (s, 3H), 5.54 (s, 2H), 7.59 (s, 1H), 7.63 (dd, 1H, J=8.2 Hz, 6.6 Hz), 7.84 (dd, 1H, J=8.2 Hz, 1.0 Hz), 7.91 (d, 1H, J=8.6 Hz), 8.26 (dd, 1H, J=8.6 Hz, 2.3 Hz), 8.63 (d, 1H, J=2.3 Hz), 8.65 (dd, 1H, J=6.6 Hz, 1.0 Hz), 10.81 (br, 1H)

EXAMPLE 1-54

6-(3,3,3-Trifluoro-2-hydroxy-2-methylpropanoylamino)-2,10,10-trioxo-5,11-dihydro[1]benzothiepino[3,4-c]pyridin-5-one (Compound 1-54) (yield: 18%)

$^1$H-NMR (DMSO-d$_6$) δ: 1.51 (s, 3H), 5.31 (s, 2H), 7.61 (br, 1H), 7.65 (d, 1H, J=6.9 Hz), 7.80–7.87 (m, 3H), 8.35 (d, 1H, J=1.6 Hz), 8.38 (dd, 1H, J=6.9 Hz, 1.6 Hz), 10.72 (br, 1H)

EXAMPLE 1-55

10,10-Dioxo-9-(3,3,3-trifluoro-2-hydroxy-2-methylpropanoylamino)-5,11-dihydro[1]benzothiepino[3,4-b]pyridin-5-one (Compound 1-55) (yield: 5%)

$^1$H-NMR (CDCl$_3$) δ: 1.78 (s, 3H), 5.26 (s, 2H), 5.83 (br, 1H), 7.41 (dd, 1H, J=8.2 Hz, 1.0 Hz), 7.55 (dd, 1H, J=7.9 Hz, 4.9 Hz), 7.74 (t, 1H, J=8.2 Hz), 8.46 (dd, 1H, J=7.9 Hz, 1.6 Hz), 8.73 (dd, 1H, J=4.9 Hz, 1.6 Hz), 8.97 (dd, 1H, J=8.2 Hz, 1.0 Hz), 11.61 (br, 1H)

EXAMPLE 2-1

9-(2,2-Dimethylpropanoylamino)-5,5-dioxo-4,10-dihydrothieno[3,2-c][1]benzothiepin-10-one (Compound 2-1) (yield: 91%)

$^1$H-NMR (DMSO-d$_6$) δ: 1.32 (s, 9H), 4.65 (s, 2H), 7.02 (d, 1H, J=5.3 Hz), 7.69 (t, 1H, J=7.6 Hz), 7.71 (d, 1H, J=5.3 Hz), 7.90 (d, 1H, J=7.6 Hz), 8.65 (d, 1H, J=7.6 Hz), 10.18 (br, 1H)

EXAMPLE 2-2

7-(2,2-Dimethylpropanoylamino)-5,5-dioxo-4,10-dihydrothieno[3,2-c][1]benzothiepin-10-one (Compound 2-2) (yield: 96%)

$^1$H-NMR (DMSO-d$_6$) δ: 1.27 (s, 9H), 5.26 (s, 2H), 7.24 (d, 1H, J=5.1 Hz), 8.03 (d, 1H, J=8.6 Hz), 8.06 (d, 1H, J=5.1 Hz), 8.27 (dd, 1H, J=8.6 Hz, 2.1 Hz), 8.52 (s, 1H), 9.98 (br, 1H)

EXAMPLE 2-3

9-(2,2-Dimethylpropanoylamino)-5,5-dioxo-8-methyl-4,10-dihydrothieno[3,2-c][1]benzothiepin-10-one (Compound 2-3) (yield: 94%)

$^1$H-NMR (DMSO-d$_6$) δ: 1.20 (s, 9H), 2.31 (s, 3H), 5.05 (s, 2H), 7.10 (d, 1H, J=5.0 Hz), 7.69 (d, 1H, J=8.6 Hz), 7.83 (d, 1H, J=8.6 Hz), 7.92 (d, 1H, J=5.0 Hz), 9.92 (br, 1H)

EXAMPLE 2-4

8-Chloro-9-(2,2-dimethylpropanoylamino)-5,5-dioxo-4,10-dihydrothieno[3,2-c][1]benzothiepin-10-one (Compound 2-4) (yield: 99%)

$^1$H-NMR (CDCl$_3$) δ: 1.31 (s, 9H), 4.67 (s, 2H), 6.99 (d, 1H, J=5.3 Hz), 7.68 (d, 1H, J=5.3Hz), 7.76 (d, 1H, J=8.4 Hz), 7.96 (d, 1H, J=8.4 Hz), 8.24 (br, 1H)

EXAMPLE 2-5

8-Chloro-7-(2,2-dimethylpropanoylamino)-5,5-dioxo-4,10-dihydrothieno[3,2-c][1]benzothiepin-10-one (Compound 2-5) (yield: 99%)

$^1$H-NMR (CDCl$_3$) δ: 1.38 (s, 9H), 4.71 (s, 2H), 7.05 (d, 1H, J=5.0 Hz), 7.73 (d, 1H, J=5.0 Hz), 8.21 (s, 1H), 8.30 (br, 1H), 9.35 (s, 1H)

EXAMPLE 2-6

9-(2,2-Dimethylpropanoylamino)-5,5-dioxo-6-methyl-4,10-dihydrothieno[3,2-c][1]benzothiepin-10-one (Compound 2-6) (yield: 98%)

$^1$H-NMR (DMSO-d$_6$) δ: 1.30 (s, 9H), 2.77 (s, 3H), 4.64 (s, 2H), 6.97 (d, 1H, J=5.1 Hz), 7.40 (d, 1H, J=8.7 Hz), 7.62 (d, 1H, J=5.1 Hz), 8.37 (d, 1H, J=8.7 Hz), 9.50 (br, 1H)

EXAMPLE 2-7

9-(2,2-Dimethylpropanoylamino)-5,5-dioxo-6-methoxy-4,10-dihydrothieno[3,2-c][1]benzothiepin-10-one (Compound 2-7) (yield: 99%)

$^1$H-NMR (DMSO-d$_6$) δ: 1.29 (s, 9H), 3.99 (s, 3H), 4.69 (s, 2H), 6.97 (d, 1H, J=5.3 Hz), 7.21 (d, 1H, J=9.2 Hz), 7.60 (d, 1H, J=5.3 Hz), 8.39 (d, 1H, J=9.2 Hz), 9.37 (br, 1H)

EXAMPLE 2-8

3-(2,2-Dimethylpropanoylamino)-5,5-dioxo-10-methoxy-6,11-dihydrodibenzo[b,e]thiepin-11-one (Compound 2-8) (yield: 89%)

$^1$H-NMR (DMSO-d$_6$) δ: 1.25 (s, 9H), 3.77 (s, 3H), 5.12 (s, 2H), 7.10 (d, 1H, J=8.2 Hz), 7.13 (d, 1H, J=8.2 Hz), 7.48 (t, 1H, J=8.2 Hz), 7.77 (d, 1H, J=8.2 Hz), 8.16 (dd, 1H, J=8.2 Hz, 2.0 Hz), 8.37 (d, 1H, J=2.0 Hz), 9.82 (br, 1H)

EXAMPLE 2-9

1-(2,2-Dimethylpropanoylamino)-5,5-dioxo-7-methoxy-6,11-dihydrodibenzo[b,e]thiepin-11-one (Compound 2-9) (yield: 90%)

$^1$H-NMR (DMSO-d$_6$) δ: 1.30 (s, 9H), 3.89 (s, 3H), 4.70 (s, 2H), 7.12 (d, 1H, J=8.2 Hz), 7.45 (t, 1H, J=8.2 Hz), 7.57 (dd, 1H, J=8.2 Hz, 1.0 Hz), 7.63 (t, 1H, J=8.2 Hz), 7.79 (dd, 1H, J=8.2 Hz, 1.0 Hz), 8.47 (dd, 1H, J=8.2 Hz, 1.0 Hz), 9.02 (br, 1H)

EXAMPLE 2-10

8-(2,2-Dimethylpropanoylamino)-5,5-dioxo-1-fluoro-6,11-dihydrodibenzo[b,e]thiepin-11-one (Compound 2-10) (yield: 99%)

$^1$H-NMR (DMSO-d$_6$) δ: 1.30 (s, 9H), 4.68 (s, 2H), 7.34–7.47 (m, 2H), 7.65 (ddd, 1H, J=8.3 Hz, 8.3 Hz, 5.0 Hz), 7.72–7.84 (m, 3H), 8.02 (d, 1H, J=8.6 Hz)

EXAMPLE 2-11

6-Chloro-9-(2,2-dimethylpropanoylamino)-5,5-dioxo-4,10-dihydrothieno[3,2-c][1]benzothiepin-10-one (Compound 2-11) (yield: 85%)

$^1$H-NMR (CDCl$_3$) δ: 1.36 (s, 9H), 4.72 (s, 2H), 6.99 (d, 1H, J=5.1 Hz), 7.60 (d, 1H, J=9.0 Hz), 7.64 (d, 1H, J=5.1 Hz), 8.48 (d, 1H, J=9.0 Hz), 9.60 (br, 1H)

EXAMPLE 2-12

9-(2,2-Dimethylpropanoylamino)-5,5-dioxo-6-fluoro-4,10-dihydrothieno[3,2-c][1]benzothiepin-10-one (Compound 2-12) (yield: 78%)

$^1$H-NMR (CDCl$_3$) δ: 1.29 (s, 9H), 4.77 (s, 2H), 7.01 (d, 1H, J=5.1 Hz), 7.36 (dd, 1H, J=9.9 Hz, 9.6 Hz), 7.68 (d, 1H, J=5.1 Hz), 8.51 (dd, 1H, J=9.6 Hz, 4.6 Hz), 9.60 (br, 1H)

EXAMPLE 3-1

9-Acetamido-5,5-dioxo-4,10-dihydrothieno[3,2-c][1]benzothiepin-10-one (Compound 3-1) (yield: 91%)

$^1$H-NMR (DMSO-d$_6$) δ: 2.02 (s, 3H), 5.15 (s, 2H), 7.13 (d, 1H, J=5.0 Hz), 7.76 (d, 1H, J=7.9 Hz), 7.78–7.87 (m, 2H), 7.96 (d, 1H, J=5.0 Hz), 10.20 (br, 1H)

EXAMPLE 3-2

1-Acetamido-5,5-dioxo-7-fluoro-6,11-dihydrodibenzo[b,e]thiepin-11-one (Compound 3-2) (yield: 89%)

$^1$H-NMR (DMSO-d$_6$) δ: 1.98 (s, 3H), 5.15 (s, 2H), 7.46–7.68 (m, 4H), 7.73–7.85 (m, 2H), 10.27 (br, 1H)

EXAMPLE 3-3

3-Acetamido-5,5-dioxo-7-fluoro-6,11-dihydrodibenzo[b,e]thiepin-11-one (Compound 3-3) (yield: 75%)

$^1$H-NMR (CDCl$_3$) δ: 1.98 (s, 3H), 5.25 (s, 2H), 7.49–7.59 (m, 2H), 7.87–8.02 (m, 3H), 8.35 (s, 1H), 10.67 (br, 1H)

EXAMPLE 3-4

5,5-Dioxo-9-trifluoroacetylamino-4,10-dihydrothieno[3,2-c][1]benzothiepin-10-one (Compound 3-4) (yield: 65%)

$^1$H-NMR (DMSO-d$_6$) δ: 4.65 (s, 2H), 7.02 (d, 1H, J=5.0 Hz), 7.66–7.72 (m, 2H), 7.91 (dd, 1H, J=7.9 Hz, 1.2 Hz), 8.66 (dd, 1H, J=7.9 Hz, 1.2 Hz), 10.19 (br, 1H)

EXAMPLE 3-5

5,5-Dioxo-7-trifluoroacetylamino-4,10-dihydrothieno[3,2-c][1]benzothiepin-10-one (Compound 3-5) (yield: 64%)

$^1$H-NMR (DMSO-d$_6$) δ: 5.30 (s, 2H), 7.25 (d, 1H, J=5.1 Hz), 8.09 (d, 1H, J=5.1 Hz), 8.13 (d, 1H, J=8.6 Hz), 8.25 (d, 1H, J=8.6 Hz), 8.52 (s, 1H), 11.95 (br, 1H)

EXAMPLE 3-6

5,5-Dioxo-9-ethoxycarbonylamino-4,10-dihydrothieno[3,2-c][1]benzothiepin-10-one (Compound 3-6) (yield: 69%)

$^1$H-NMR (DMSO-d$_6$) δ: 1.21 (t, 3H, J=7.3 Hz), 4.07 (q, 2H, J=7.3 Hz), 5.18 (s, 2H), 7.15 (d, 1H, J=5.0 Hz), 7.33–7.93 (m, 3H), 8.02 (d, 1H, J=5.0 Hz), 9.71 (br, 1H)

EXAMPLE 3-7

5,5-Dioxo-9-(2-hydroxyacetylamino)-4,10-dihydrothieno[3,2-c][1]benzothiepin-10-one (Compound 3-7) (yield: 83%)

$^1$H-NMR (DMSO-d$_6$) δ: 4.00 (d, 1H, J=5.6 Hz), 5.17 (s, 2H), 6.20 (t, 1H, J=5.6 Hz), 7.19 (d, 1H, J=5.0 Hz), 7.79–7.90 (m, 2H), 8.03 (d, 1H, J=9.0 Hz), 8.66 (dd, 1H, J=7.9 Hz, 1.6 Hz), 10.67 (br, 1H)

EXAMPLE 3-8

5,5-Dioxo-9-(2-chloroacetylamino)-4,10-dihydrothieno[3,2-c][1]benzothiepin-10-one (Compound 3-8) (yield: 88%)

$^1$H-NMR (DMSO-d$_6$) δ: 4.29 (s, 2H), 5.16 (s, 2H), 7.16 (d, 1H, J=5.0 Hz), 7.82 (t, 1H, J=7.9 Hz), 7.91 (dd, 1H, J=7.9 Hz, 1.3 Hz), 7.99 (d, 1H, J=5.0 Hz), 8.06 (dd, 1H, J=7.9 Hz, 1.3 Hz), 10.54 (br, 1H)

EXAMPLE 3-9

5,5-Dioxo-9-(2-tetrahydrofuroylamino)-4,10-dihydrothieno[3,2-c][1]benzothiepin-10-one (Compound 3-9) (yield: 86%)

$^1$H-NMR (DMSO-d$_6$) δ: 1.80–2.05 (m, 3H), 2.15–2.28 (m, 1H), 3.92 (dd, 1H, J=7.9 Hz, 6.9 Hz), 4.05 (dd, 1H, J=12.8 Hz, 6.9 Hz), 4.44 (dd, 1H, J=8.4 Hz, 4.4 Hz), 5.16 (d, 1H, J=17.8 Hz), 5.24 (d, 1H, J=17.8 Hz), 7.18 (d, 1H, J=5.0 Hz), 7.80–7.85 (m, 2H), 8.05 (d, 1H, J=5.0 Hz), 8.40 (d, 1H, J=9.5 Hz), 10.49 (br, 1H)

EXAMPLE 3-10

5,5-Dioxo-9-(3-tetrahydrofuroylamino)-4,10-dihydrothieno[3,2-c][1]benzothiepin-10-one (Compound 3-10) (yield: 89%)

$^1$H-NMR (DMSO-d$_6$) δ: 2.00–2.08 (m, 2H), 3.09–3.20 (m, 1H), 3.65–3.75 (m, 3H), 3.90 (t, 1H, J=8.2 Hz), 5.14 (s, 2H), 7.13 (d, 1H, J=5.0 Hz), 7.70 (dd, 1H, J=7.9 Hz, 1.7 Hz), 7.78 (t, 1H, J=7.9 Hz), 7.86 (dd, 1H, J=7.9 Hz, 1.7 Hz), 7.95 (d, 1H, J=5.0 Hz), 10.37 (br, 1H)

EXAMPLE 3-11

9-(2-Bromo-2-methylpropanoylamino)-5,5-dioxo-4,10-dihydrothieno[3,2-c][1]benzothiepin-10-one (Compound 3-11) (yield: 93%)

$^1$H-NMR (DMSO-d$_6$) δ: 1.96 (s, 6H), 5.18 (s, 2H), 7.17 (d, 1H, J=5.0 Hz), 7.84 (t, 1H, J=7.9 Hz), 7.90 (dd, 1H, J=7.9 Hz, 1.7 Hz), 8.00 (d, 1H, J=5.0 Hz), 8.05 (d, 1H, J=7.9 Hz), 10.43 (br, 1H)

EXAMPLE 3-12

5,5-Dioxo-9-(2-hydroxy-2-methylpropanoylamino)-4,10-dihydrothieno[3,2-c][1]benzothiepin-10-one (Compound 3-12) (yield: 72%)

$^1$H-NMR (DMSO-d$_6$) δ: 1.32 (s, 6H), 5.21 (s, 2H), 6.04 (br, 1H), 7.18 (d, 1H, J=5.0 Hz), 7.82–7.84 (m, 2H), 8.51 (d, 1H, J=9.5 Hz), 10.71 (br, 1H)

EXAMPLE 3-13

5,5-Dioxo-1-(2-hydroxy-2-methylpropanoylamino)-8-methoxy-6,11-dihydrodibenzo[b,e]thiepin-11-one (Compound 3-13) (yield: 88%)

$^1$H-NMR (DMSO-d$_6$) δ: 1.29 (s, 6H), 3.85 (s, 3H), 5.25 (s, 2H), 6.03 (s, 1H), 6.99 (d, 1H, J=2.6 Hz), 7.14 (dd, 1H, J=8.9 Hz, 2.6 Hz), 7.70–7.80 (m, 2H), 7.90 (d, 1H, J=8.9Hz), 8.28 (dd, 1H, J=7.6 Hz, 1.7 Hz), 10.06 (br, 1H)

EXAMPLE 3-14

5,5-Dioxo-9-(2-hydroxy-2-methylbutanoylamino)-4,10-dihydrothieno[3,2-c][1]benzothiepin-10-one (Compound 3-14) (yield: 58%)

$^1$H-NMR (DMSO-d$_6$) δ: 0.78 (t, 3H, J=7.3 Hz), 1.31 (s, 3H), 1.51 (dt, 1H, J=14.2 Hz, 7.3Hz), 1.71 (dt, 1H, J=14.3 Hz, 7.3 Hz), 5.21 (s, 2H), 5.85 (br, 1H), 7.18 (d, 1H, J=5.1 Hz), 7.80–7.87 (m, 2H), 8.06 (d, 1H, J=5.1 Hz), 8.51 (d, 1H, J=8.6 Hz), 10.69 (br, 1H)

EXAMPLE 3-15

5,5-Dioxo-9-(1-hydroxycyclopropanecarbonylamino)-4,10-dihydrothieno[3,2-c][1]benzothiepin-10-one (Compound 3-15) (yield: 41%)

$^1$H-NMR (DMSO-d$_6$) δ: 1.00–1.08 (m, 2H), 1.11–1.18 (m, 2H), 5.19 (s, 2H), 6.82 (br, 1H), 7.19 (d, 1H, J=5.0 Hz), 7.82–7.88 (m, 2H), 8.05 (d, 1H, J=5.0 Hz), 8.57 (d, 1H, J=7.9 Hz), 10.71 (br, 1H)

EXAMPLE 3-16

5,5-Dioxo-9-(2-hydroxy-3-methylbutanoylamino)-4,10-dihydrothieno[3,2-c][1]benzothiepin-10-one (Compound 3-16) (yield: 99%)

$^1$H-NMR (DMSO-d$_6$) δ: 0.77 (d, 3H, J=6.6 Hz), 0.97 (d, 3H, J=6.6 Hz), 1.98–2.05 (m, 1H), 3.91 (br, 1H), 5.18 (s, 2H), 6.12 (br, 1H), 7.18 (d, 1H, J=5.0 Hz), 7.78–7.83 (m, 2H), 8.03 (d, 1H, J=8.6 Hz), 8.56 (d, 1H, J=8.6 Hz), 10.61 (br, 1H)

EXAMPLE 3-17

9-(2-Cyclohexyl-2-hydroxyacetylamino)-5,5-dioxo-4,10-dihydrothieno[3,2-c][1]benzothiepin-10-one (Compound 3-17) (yield: 97%)

$^1$H-NMR (DMSO-d$_6$) δ: 1.15–1.50 (m, 5H), 1.65–1.85 (m, 5H), 2.98–3.18 (m, 1H), 4.11–4.16 (m, 1H), 4.67 (s, 2H), 7.01 (d, 1H, J=5.0 Hz), 7.65–7.74 (m, 2H), 7.93 (d, 1H, J=8.2 Hz), 10.61 (br, 1H)

EXAMPLE 3-18

5,5-Dioxo-9-(3-hydroxy-4,4,4-trifluoro-3-methylbutanoylamino-4,10-dihydrothieno[3,2-c][1]benzothiepin-10-one (Compound 3-18) (yield: 99%)

$^1$H-NMR (DMSO-d$_6$) δ: 1.41 (s, 3H), 2.54 (d, 1H, J=14.3 Hz), 2.70 (d, 1H, J=14.3Hz), 5.19 (s, 2H), 6.41 (br, 1H), 7.15 (d, 1H, J=5.0 Hz), 7.78–7.87 (m, 2H), 7.98 (dd, 1H, J=7.8 Hz, 1.8 Hz), 8.02 (d, 1H, J=5.0 Hz), 10.31 (br, 1H)

EXAMPLE 3-19

5,5-Dioxo-9-(3-hydroxy-4,4,4-trifluoro-3-trifluoromethylbutanoylamino)-4,10-dihydrothieno[3,2-c][1]benzothiepin-10-one (Compound 3-19) (yield: 80%)

$^1$H-NMR (DMSO-d$_6$) δ: 3.02 (s, 2H), 5.11 (s, 2H), 7.16 (d, 1H, J=5.0 Hz), 7.81 (t, 1H, J=7.9 Hz), 7.93 (dd, 1H, J=7.9 Hz, 1.3 Hz), 7.96 (d, 1H, J=5.0 Hz), 8.00 (d, 1H, J=7.9 Hz), 8.35 (br, 1H), 10.52 (br, 1H)

EXAMPLE 3-20

9-(2-Amino-2-methylpropanoylamino)-5,5-dioxo-4,10-dihydrothieno[3,2-c][1]benzothiepin-10-one (Compound 3-20) (yield: 75%)

$^1$H-NMR (DMSO-d$_6$) δ: 1.43 (s, 6H), 4.63 (s, 2H), 7.01 (d, 1H, J=5.0 Hz), 7.65–7.72 (m, 2H), 7.91 (dd, 1H, J=7.7 Hz, 1.2 Hz), 8.67 (dd, 1H, J=7.7 Hz, 1.2 Hz), 11.50 (br, 1H)

EXAMPLE 3-21

5,5-Dioxo-9-(2-furoylamino)-4,10-dihydrothieno[3,2-c][1]benzothiepin-10-one (Compound 3-21) (yield: 76%)

$^1$H-NMR (DMSO-d$_6$) δ: 5.20 (s, 2H), 6.71 (dd, 1H, J=3.3 Hz, 1.7 Hz), 7.17 (d, 1H, J=5.0 Hz), 7.30 (d, 1H, J=3.3 Hz), 7.85 (t, 1H, J=7.9 Hz), 7.91 (d, 1H, J=7.9 Hz), 7.98 (d, 1H, J=1.0 Hz), 8.02 (d, 1H, J=5.0 Hz), 8.28 (d, 1H, J=7.9 Hz), 10.74 (br, 1H)

EXAMPLE 3-22

5,5-Dioxo-9-(3-furoylamino)-4,10-dihydrothieno[3,2-c][1]benzothiepin-10-one (Compound 3-22) (yield: 83%)

$^1$H-NMR (DMSO-d$_6$) δ: 5.17 (s, 2H), 6.89 (d, 1H, J=2.0 Hz), 7.15 (d, 1H, J=5.0 Hz), 7.77 (d, 1H, J=2.0 Hz), 7.80–7.98 (m, 4H), 8.32 (s, 1H), 10.44 (br, 1H)

EXAMPLE 3-23

5,5-Dioxo-9-(2-hydroxy-2-phenylacetylamino)-4,10-dihydrothieno[3,2-c][1]benzothiepin-10-one (Compound 3-23) (yield: 67%)

$^1$H-NMR (DMSO-d$_6$) δ: 5.12 (d, 1H, J=4.0 Hz), 5.18 (d, 1H, J=18.3 Hz), 5.28 (d, 1H, J=18.3 Hz), 6.92 (d, 1H, J=4.0Hz), 7.19 (d, 1H, J=5.0Hz), 7.24–7.35 (m, 3H), 7.43 (d, 2H, J=7.6 Hz), 7.82–7.87 (m, 2H), 8.12 (d, 1H, J=5.0 Hz), 8.44 (dd, 1H, J=9.2Hz, 3.6 Hz), 10.78 (br, 1H)

EXAMPLE 3-24

9-(5-Chloro-2-hydroxybenzoylamino)-5,5-dioxo-4,10-dihydrothieno[3,2-c][1]benzothiepin-10-one (Compound 3-24) (yield: 81%)

$^1$H-NMR (DMSO-d$_6$) δ: 5.21 (s, 2H), 6.04 (br, 1H), 7.18 (d, 1H, J=5.0 Hz), 7.82–7.84 (m, 2H), 8.51 (d, 1H, J=9.5 Hz), 10.71 (br, 1H)

EXAMPLE 3-25

5,5-Dioxo-9-(3-hydroxy-2-pyridylcarbonylamino)-4,10-dihydrothieno[3,2-c][1]benzothiepin-10-one (Compound 3-25) (yield: 84%)

$^1$H-NMR (DMSO-d$_6$) δ: 4.68 (s, 2H), 7.02 (d, 1H, J=5.0 Hz), 7.36 (dd, 1H, J=8.3 Hz, 1.3 Hz), 7.45 (dd, 1H, J=8.3 Hz, 4.3 Hz), 7.70 (d, 1H, J=5.0 Hz), 7.77 (t, 1H, J=8.3 Hz), 8.01 (dd, 1H, J=8.3 Hz, 1.5Hz), 8.32 (dd, 1H, J=4.3 Hz, 1.3 Hz), 8.79 (dd, 1H, J=8.3 Hz, 1.5 Hz), 11.48 (br, 1H), 11.96 (br, 1H)

EXAMPLE 3-26

9-(3,3-Dimethylureido)-5,5-dioxo-4,10-dihydrothieno[3,2-c][1]benzothiepin-10-one (Compound 3-26) (yield: 77%)

$^1$H-NMR (DMSO-d$_6$) δ: 2.63 (s, 6H), 5.20 (s, 2H), 7.14 (d, 1H, J=5.3 Hz), 7.69–7.78 (m, 2H), 8.03 (d, 1H, J=5.3 Hz), 8.08 (dd, 1H, J=7.6 Hz, 2.3Hz), 9.23 (br, 1H)

EXAMPLE 3-27

5,5-Dioxo-9-(4-morpholinocarbonylamino)-4,10-dihydrothieno[3,2-c][1]benzothiepin-10-one (Compound 3-27) (yield: 65%)

$^1$H-NMR (DMSO-d$_6$) δ: 3.40 (t, 4H, J=4.5 Hz), 3.64 (t, 4H, J=4.5 Hz), 5.17 (s, 2H), 7.12 (d, 1H, J=5.0 Hz), 7.72–7.74 (m, 2H), 7.79–7.83 (m, 1H), 7.99 (d, 1H, J=5.0 Hz), 9.28 (br, 1H)

EXAMPLE 3-28

5,5-Dioxo-9-(3-(1,2,2-trimethylpropyl)ureido)-4,10-dihydrothieno[3,2-c][1]benzothiepin-10-one (Compound 3-28) (yield: 32%)

$^1$H-NMR (DMSO-d$_6$) δ: 0.89 (s, 9H), 1.03 (d, 3H, J=6.6 Hz), 3.53–3.61 (m, 1H), 5.00 (s, 2H), 7.14 (br, 1H), 7.15 (d, 1H, J=5.2 Hz), 7.63 (t, (H, J=7.6 Hz), 7.90 (d, 1H, J=5.2 Hz), 8.32 (dd, 1H, J=7.6 Hz, 1.7 Hz)

EXAMPLE 3-29

5,5-Dioxo-9-(3-(2-hydroxyethyl)-3-methylureido)-4,10-dihydrothieno[3,2-c][1]benzothiepin-10-one (Compound 3-29) (yield: 38%)

$^1$H-NMR (CDCl$_3$) δ: 3.15 (s, 3H), 3.58 (t, 2H, J=5.0 Hz), 3.85 (t, 2H, J=5.0 Hz), 4.65 (s, 2H), 7.01 (d, 1H, J=5.0 Hz), 7.65 (t, 1H, J=7.9 Hz), 7.70 (d, 1H, J=5.0 Hz), 7.85 (d, 1H, J=7.9 Hz), 8.55 (d, 1H, J=7.9 Hz), 9.83 (br, 1H)

EXAMPLE 3-30

5,5-Dioxo-6-(tert-butoxycarbonylamino)-4,10-dihydrothieno[3,2-c][1]benzothiepin-10-one (Compound 3-30) (yield: 73%)

$^1$H-NMR (CDCl$_3$) δ: 1.54 (s, 9H), 4.79 (s, 2H), 6.98 (d, 1H, J=5.3 Hz), 7.47 (d, 1H, J=8.0Hz), 7.61–7.67 (m, 2H), 8.69 (d, 1H, J=8.0 Hz), 9.82 (br, 1H)

EXAMPLE 3-31

5,5-Dioxo-9-(2-ethyl-2-hydroxybutanoylamino)-4,10-dihydrothieno[3,2-c][1]benzothiepin-10-one (Compound 3-30) (yield: 64%)

$^1$H-NMR (DMSO-d$_6$) δ: 0.80 (t, 6H, J=7.6 Hz), 1.47–1.61 (m, 2H), 1.68–1.81 (m, 2H), 5.16 (s, 2H), 5.52 (br, 1H), 7.17 (d, 1H, J=5.0 Hz), 7.77–7.84 (m, 2H), 8.01 (d, 1H, J=5.0 Hz), 8.52 (dd, 1H, J=8.3 Hz, 2.3 Hz), 10.66 (br, 1H)

EXAMPLE 3-32

5,5-Dioxo-9-(3-methoxypropanoylamino)-4,10-dihydrothieno[3,2-c][1]benzothiepin-10-one (Compound 3-32) (yield: 94%)

$^1$H-NMR (CDCl$_3$) δ: 2.68 (t, 2H, J=5.6 Hz), 3.51 (s, 3H), 3.71 (t, 2H, J=5.6 Hz), 4.64 (s, 2H), 7.01 (d, 1H, J=5.1 Hz), 7.68 (t, 1H, J=7.9 Hz), 7.70 (d, 1H, J=5.1 Hz), 7.90 (d, 1H, J=7.9 Hz), 8.65 (d, 1H, J=7.9 Hz), 10.20 (br, 1H)

PREPARATION EXAMPLE 1

Tablets

Tablets having the following composition were prepared according to a conventional method.

| | |
|---|---|
| Compound 1-25 | 5 mg |
| Lactose | 60 mg |
| Potato starch | 30 mg |
| Polyvinyl alcohol | 2 mg |
| Magnesium stearate | 1 mg |
| Tar pigment | Trace |

PREPARATION EXAMPLE 2

Powder

Powder having the following composition was prepared according to a conventional method.

| | |
|---|---|
| Compound 1-1 | 5 mg |
| Lactose | 280 mg |

PREPARATION EXAMPLE 3

Syrup

Syrup having the following composition was prepared according to a conventional method.

| | |
|---|---|
| Compound 1-25 | 5 mg |
| Refined sugar | 40 g |
| Ethyl p-hydroxybenzoate | 40 mg |
| Propyl p-hydroxybenzoate | 10 mg |
| Strawberry flavor | 0.1 cc |

Water is added to make a volume of 100 cc.

Industrial Applicability

The present invention can provide novel tricyclic compounds which are useful as therapeutic agents for pollakiuria and urinary incontinence.

What is claimed is:

1. A tricyclic compound represented by general formula (I):

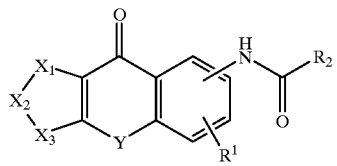

(I)

(wherein
  $R^1$ represents hydrogen, substituted or unsubstituted lower alkyl, substituted or unsubstituted lower alkoxy or halogen;
  $X^1$—$X^2$—$X^3$ represents $CR^5$=$CR^6$—$CR^7$=$CR^8$ (wherein $R^5$, $R^6$, $R^7$ and $R^8$, which may be the same or different, each represents hydrogen, substituted or unsubstituted lower alkyl, hydroxy, substituted or unsubstituted lower alkoxy, nitro, amino, lower monoalkyl-substituted amino, lower dialkyl-substituted amino, substituted or unsubstituted lower alkanoylamino or halogen), $N(O)m$=$CR^5$—$CR^6$=$CR^7$ (wherein $R^5$, $R^6$ and $R^7$ have the same significances as defined above, and m represents 0 or 1), $CR^5$=$CR^6$—$N(O)m$=$CR^7$ (wherein $R^5$, $R^6$, $R^7$ and m have the same significances as defined above), $CR^5$=$CR^6$—$CR^7$=$N(O)m$ (wherein $R^5$, $R^6$, $R^7$ and m have the same significances as defined above), $CR^5$=$CR^6$—O (wherein $R^5$ and $R^6$ have the same significances as defined above), $CR^5$=$CR^6$—S (wherein $R^5$ and $R^6$ have the same significances as defined above), O—$CR^7$=$CR^8$ (wherein $R^7$ and $R^8$ have the same significances as defined above), S—$CR^7$=$CR^8$ (wherein $R^7$ and $R^8$ have the same significances as defined above) or O—$CR^7$=N (wherein $R^7$ has the same significance as defined above); and when $R^2$ represents hydrogen, substituted or unsubstituted lower alkyl, substituted or unsubstituted lower alkenyl, trifluoromethyl, substituted or unsubstituted lower alkoxy, amino, substituted or unsubstituted lower monoalkyl-substituted amino, substituted or unsubstituted lower dialkyl-substituted amino, substituted or unsubstituted aryl, substituted or unsubstituted heteroaryl, substituted or unsubstituted aralkylamino, substituted or unsubstituted arylamino, a substituted or unsubstituted alicyclic heterocyclic group, a substituted or unsubstituted N-substituted heterocyclic group or

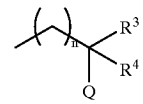

(wherein
  n is 0 or 1; $R^3$ and $R^4$, which may be the same or different, each represents hydrogen, substituted or unsubstituted lower alkyl, substituted or unsubstituted cyclic alkyl, substituted or unsubstituted aryl, substituted or unsubstituted aralkyl or trifluoromethyl, or $R^3$ and $R^4$ may be combined together to form cyclic alkyl; and Q represents hydroxy, substituted or unsubstituted lower alkoxy, amino or halogen),
  Y represents —$CH_2SO_2$—, —$SCH_2$—, —$SOCH_2$— or —$SO_2CH_2$—; when $R^2$ represents hydrogen, substituted or unsubstituted lower alkenyl, trifluoromethyl, substituted or unsubstituted lower alkoxy, amino, substituted or unsubstituted lower monoalkyl-substituted amino, substituted or unsubstituted lower dialkyl-substituted amino, substituted or unsubstituted aryl, substituted or unsubstituted heteroaryl, substituted or unsubstituted aralkylamino, substituted or unsubstituted arylamino, a substituted or unsubstituted alicyclic heterocyclic group, a substituted or unsubstituted N-substituted heterocyclic group or

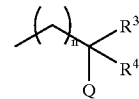

(wherein
  n, $R^3$, $R^4$ and Q have the same significances as defined above),
  Y represents —$OCH_2$—);
or a pharmaceutically acceptable salt thereof.

2. A tricyclic compound or a pharmaceutically acceptable salt thereof according to claim 1, wherein $R^1$ is hydrogen, substituted or unsubstituted lower alkoxy or halogen.

3. A tricyclic compound or a pharmaceutically acceptable salt thereof according to claim 2, wherein $R^1$ is hydrogen.

4. A tricyclic compound or a pharmaceutically acceptable salt thereof according to claim 1, wherein Y is —$CH_2SO_2$—, —$SO_2CH_2$— or —$OCH_2$—.

5. A tricyclic compound or a pharmaceutically acceptable salt thereof according to claim 4, wherein Y is —$CH_2SO_2$— or —$SO_2CH_2$—.

6. A tricyclic compound or a pharmaceutically acceptable salt thereof according to claim 5, wherein Y is —$CH_2SO_2$—.

7. A tricyclic compound or a pharmaceutically acceptable salt thereof according to claim 1, wherein $X^1$—$X^2$—$X^3$ is S—$CR^7$=$CR^8$ (wherein $R^7$ and $R^8$ have the same significances as defined above).

8. A tricyclic compound or a pharmaceutically acceptable salt thereof according to claim 7, wherein $R^1$ is hydrogen and Y is —$CH_2SO_2$—.

9. A tricyclic compound or a pharmaceutically acceptable salt thereof according to claim 1, wherein $X^1$—$X^2$—$X^3$ is $CR^5$=$CR^6$—$CR^7$=$CR^8$ (wherein $R^5$, $R^6$, $R^7$ and $R^8$ have the same significances as defined above).

10. A tricyclic compound or a pharmaceutically acceptable salt thereof according to claim 9, wherein $R^1$ is hydrogen and Y is —$CH_2SO_2$—.

11. A tricyclic compound or a pharmaceutically acceptable salt thereof according to any of claims 1 to 10, wherein $R^2$ is

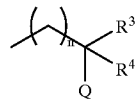

(wherein n, $R^3$, $R^4$ and Q have the same significances as defined above).

12. A tricyclic compound or a pharmaceutically acceptable salt thereof according to claim 11, wherein n is 0.

13. A tricyclic compound or a pharmaceutically acceptable salt thereof according to claim 12, wherein $R^3$ is methyl, $R^4$ is trifluoromethyl, and Q is hydroxy.

14. A tricyclic compound or a pharmaceutically acceptable salt thereof according to claim 1, wherein $R^1$ is hydrogen, Y is —$CH_2SO_2$—, $X^1$—$X^2$—$X^3$ is S—$CR^7$=$CR^8$ (wherein $R^7$ and $R^8$ have the same significances as defined above), $R^3$ is methyl, $R^4$ is trifluoromethyl, and Q is hydroxy.

15. A pharmaceutical composition comprising a tricyclic compound or a pharmaceutically acceptable salt thereof according to claim 1.

* * * * *